US012697227B2

(12) United States Patent
Pamu et al.

(10) Patent No.: US 12,697,227 B2
(45) Date of Patent: Aug. 4, 2026

(54) IMPLANTS FOR FULL CONSTRAINT OF PYRAMESH T-CAGE

(71) Applicant: Warsaw Orthopedic, Inc., Warsaw, IN (US)

(72) Inventors: Deepika Pamu, District Hyderabad (IN); Lakshmi Soujanya Nallamothu, Hyderabad (IN); Vidya Sagarika Kandregula, Hyderabad (IN); Harika Cattamanchi, Hyderabad (IN); Srikanth Ganti, Hyderabad (IN); Subrat Samantray, Bangalore (IN)

(73) Assignee: WARSAW ORTHOPEDIC, INC., Warsaw, IN (US)

( * ) Notice: Subject to any disclaimer, the term of this patent is extended or adjusted under 35 U.S.C. 154(b) by 0 days.

(21) Appl. No.: 18/975,348

(22) Filed: Dec. 10, 2024

(65) Prior Publication Data

US 2025/0195237 A1     Jun. 19, 2025

Related U.S. Application Data

(60) Provisional application No. 63/610,206, filed on Dec. 14, 2023.

(51) Int. Cl.
*A61F 2/44*          (2006.01)
*A61B 17/16*         (2006.01)
          (Continued)

(52) U.S. Cl.
CPC .......... *A61F 2/446* (2013.01); *A61B 17/1671* (2013.01); *A61B 17/1757* (2013.01);
          (Continued)

(58) Field of Classification Search
CPC ............ A61B 17/8042; A61B 17/1671; A61B 17/1757; A61B 17/70; A61B 17/7074;
          (Continued)

(56) References Cited

U.S. PATENT DOCUMENTS 5,776,197 A * 7/1998 Rabbe ................... A61B 17/70
                                                606/264
6,086,613 A * 7/2000 Camino ............... A61F 2/4465
                                                623/17.16
          (Continued)

FOREIGN PATENT DOCUMENTS

DE          19504867 C1     2/1996
EP          2108340 B1      9/2011
          (Continued)

OTHER PUBLICATIONS

European Search Report in Application No. 24218131.1 dated Apr. 22, 2025.

*Primary Examiner* — Marcela I. Shirsat
(74) *Attorney, Agent, or Firm* — FOX ROTHSCHILD LLP

(57) ABSTRACT

A multi-level vertebral implant comprising a biocompatible cage disposed between a first and a second endplate configured to maximize subsidence and bone contact with adjacent vertebrae is disclosed. In some embodiments, the multi-level vertebral implant comprises a first and a second endplate having plurality of anti-migration features on the bone contacting surfaces of the endplates. In various embodiments, the endplates may be configured to prevent radial and axial rotations of biocompatible cage. In various embodiments, each endplates further comprise and anterior plate that is configured to provide anchoring of the multi-level vertebral implant to ventral surfaces of the adjacent vertebrae to prevent migration of the multi-level vertebral implant in an installed state.

20 Claims, 16 Drawing Sheets

(51) Int. Cl.

| | |
|---|---|
| *A61B 17/17* | (2006.01) |
| *A61B 17/70* | (2006.01) |
| *A61F 2/30* | (2006.01) |
| *A61F 2/46* | (2006.01) |

(52) U.S. Cl.
CPC ....... *A61B 17/7074* (2013.01); *A61B 17/7082* (2013.01); *A61F 2002/30113* (2013.01); *A61F 2002/30235* (2013.01); *A61F 2002/30476* (2013.01); *A61F 2002/30507* (2013.01); *A61F 2002/30576* (2013.01); *A61F 2002/30578* (2013.01); *A61F 2002/30593* (2013.01); *A61F 2002/30599* (2013.01); *A61F 2002/30604* (2013.01); *A61F 2/30749* (2013.01); *A61F 2002/30772* (2013.01); *A61F 2002/30774* (2013.01); *A61F 2002/30784* (2013.01); *A61F 2002/30787* (2013.01); *A61F 2002/30841* (2013.01); *A61F 2002/30904* (2013.01); *A61F 2002/3092* (2013.01); *A61F 2002/3093* (2013.01); *A61F 2/442* (2013.01); *A61F 2002/4435* (2013.01); *A61F 2/4455* (2013.01); *A61F 2/4465* (2013.01); *A61F 2002/4495* (2013.01); *A61F 2/4611* (2013.01)

(58) Field of Classification Search
CPC ....... A61B 17/7082; A61B 2018/00339; A61F 2/30749; A61F 2/4455; A61F 2/4465; A61F 2/44; A61F 2/442; A61F 2/446; A61F 2/46; A61F 2/4611; A61F 2002/4435; A61F 2002/30113; A61F 2002/30235; A61F 2002/30331; A61F 2002/30383; A61F 2002/30476; A61F 2002/305; A61F 2002/30517; A61F 2002/30576; A61F 2002/30578; A61F 2002/30593; A61F 2002/30599; A61F 2002/30604; A61F 2002/30772; A61F 2002/30784; A61F 2002/30787; A61F 2002/30841; A61F 2002/30904; A61F 2002/3092; A61F 2002/3093; A61F 2002/4495

USPC ........................................... 623/17.11–17.16
See application file for complete search history.

(56) References Cited

U.S. PATENT DOCUMENTS

| | | | | |
|---|---|---|---|---|
| 2002/0099443 | A1 | 7/2002 | Messerli et al. | |
| 2004/0068318 | A1* | 4/2004 | Coates ..................... | A61F 2/44 |
| | | | | 623/17.11 |
| 2008/0312742 | A1 | 12/2008 | Abernathie | |
| 2011/0098820 | A1 | 4/2011 | Blackwell et al. | |
| 2012/0232659 | A1 | 9/2012 | Himmelberger et al. | |
| 2015/0032210 | A1 | 1/2015 | Stinchfield et al. | |
| 2016/0095711 | A1 | 4/2016 | Castro | |
| 2018/0098861 | A1 | 4/2018 | Howard et al. | |
| 2019/0029842 | A1 | 1/2019 | Xiao et al. | |
| 2019/0358055 | A1 | 11/2019 | Arnold et al. | |
| 2021/0077268 | A1* | 3/2021 | Struck ................... | A61F 2/3094 |
| 2023/0240857 | A1 | 8/2023 | Dewey et al. | |
| 2024/0407926 | A1* | 12/2024 | Biedermann ......... | A61F 2/4455 |

FOREIGN PATENT DOCUMENTS

| | | | |
|---|---|---|---|
| WO | 9932055 | A1 | 7/1999 |
| WO | 2005070346 | A1 | 8/2005 |
| WO | 2017119862 | A1 | 7/2017 |

\* cited by examiner

100

100

20

28

32

29

Z

X

Y

100

IMPLANTS FOR FULL CONSTRAINT OF PYRAMESH T-CAGE

CROSS-REFERENCE TO RELATED APPLICATION

This application claims the benefit of and priority to U.S. Provisional Patent Application No. 63/610,206 filed Dec. 14, 2023, the entire disclosure of which is incorporated by reference herein.

FIELD

The present technology is generally related to, for example, to spinal stabilization systems, and more particularly, to a multiple level vertebral implant assembly having endplates for stabilizing the assembly. Embodiments of the devices and methods are described below with reference to the Figures.

BACKGROUND

It is sometimes necessary to remove one or more vertebrae or a portion of one or more vertebrae from the human spine in response to various pathologies. For example, one or more vertebrae may become damaged as a result of tumor growth. Removal, or excision, of a vertebra, may be referred to as a vertebrectomy. Excision of a generally anterior portion of a vertebra, or vertebral body, may be referred to as a corpectomy. An implant is usually placed between the remaining vertebrae to provide structural support for the spine as a part of a corpectomy or vertebrectomy. The implant inserted between the vertebrae may be designed to facilitate fusion or to provide spinal stability between the remaining vertebrae. A successful procedure may decrease pain, preserve or enhance neurological function, and allow a patient greater mobility without an external orthosis. All or part of more than one vertebra may be damaged and require removal and replacement in some circumstances.

Non-surgical treatments, such as medication, rehabilitation, and exercise can be effective, however, they may fail to relieve the symptoms associated with these disorders. Surgical treatment of these spinal disorders includes fusion, fixation, corpectomy, discectomy, laminectomy, and implantable prosthetics. In procedures such as, for example, corpectomy and discectomy, fusion and fixation treatments may be performed that employ implants to restore the mechanical support function of vertebrae. This disclosure describes an improved corpectomy, vertebrectomy, hemi-vertebrectomy, or other vertebral implant. In some embodiments, such implants may span multiple vertebral levels.

SUMMARY

The techniques of this disclosure generally relate to a multi-level vertebral implant with metallic endplates and a polymeric body. In one aspect, the implant comprises a biocompatible cage; and a first endplate and a second endplate that each comprise: (i) a bone contacting surface that is inclined with respect to a supporting surface disposed opposite from the bone contacting surface; (ii) a plurality of anti-migration features extending from each bone contacting surface and being configured to contact an adjacent vertebrae, respectively; (iii) a cage holder extending away from each support surface, each cage holder comprising a hollow protrusion defining a fusion aperture that extends through the bone contacting surface and supporting surface of each respective endplate; (iv) an anterior plate extending orthogonally from each bone contacting surface and having at least one bone screw aperture configured to support a bone screw for anchoring into a ventral surface of a corresponding adjacent vertebrae; and (v) a plurality of anti-rotation slots disposed around each corresponding cage holder and extending through the bone contacting surface and supporting surface of each respective endplate; wherein the biocompatible cage comprises a body that extends in a longitudinal direction from a first end to a second end and has a hollow interior, wherein the first end of the body is configured to couple to the cage holder of the first endplate and the second end of the body is configured to couple to the cage holder of the second endplate, wherein the first end of the body comprises a plurality of protrusions configured to interface with the anti-rotation slots of the first endplate and the second end of the body comprises a plurality of protrusions configured to interface with the anti-rotation slots of the second endplate to thereby suppress radial movement of the biocompatible cage, and wherein the body comprises a mesh pattern including a plurality of apertures extending through a sidewall of the body that are configured to facilitate bone growth and fusion.

In another embodiment, the biocompatible cage may extend for a distance sufficient to span at least two vertebral levels for performing a corpectomy procedure. In some embodiments, each anterior plate may further comprise a locking mechanism configured to keep a corresponding bone screw from backing out, the locking mechanism comprising a locking cap, a locking slot, and a groove configured to receive a notch of the locking cap. In some embodiments, the locking cap may further comprise a plate, a cylinder extending longitudinally from a surface of the plate, a core extending through the cylinder and the plate, and the notch on the surface of the plate, wherein the cylinder is configured to be inserted into an aperture of the locking slot, wherein the notch is configured to be disposed in the groove of the locking slot in a locked position, and wherein the core is configured to receive an inserter tool and provide a resistive force when rotated about a longitudinal axis to displace the notch from the groove and to move the locking cap between the locked position and an unlocked position.

In some embodiments, each of the at least one apertures may be configured to support a corresponding bone screw at an angle between 0° to 40° along a sagittal plane in a cranial direction and between 0° to 40° along the sagittal plane in a caudal direction. In other embodiments, each of the at least one apertures may be configured to support a corresponding bone screw at an angle between −20° to 20° along a transverse plane in a lateral direction. In various embodiments, the fusion aperture may comprise a circular, an oval, or an elliptical shape and the fusion aperture communicates with the hollow interior of the biocompatible cage to facilitate boney ingrowth and spinal fusion.

In other embodiments, the circular fusion aperture may comprise a diameter of about 0.25 cm and about 0.40 cm. In other embodiments, the oval or the elliptical fusion aperture may comprise a major diameter of about 0.90 cm and about 1.10 cm, and a minor diameter of about 0.55 cm and about 0.70 cm. In various embodiments, a centerpoint of each fusion aperture and a centerpoint of the adjacent corresponding cage holder 23 may be co-axially aligned. In some embodiments, the cage holder may be about 0.50 cm and about 1.20 cm in length. In other embodiments, each bone contacting surface may be inclined at an angle of about 0° to about 6°.

In various embodiments, the plurality of anti-migration features of the first endplate may comprise a plurality of serrations that are oriented at an angle of about 15° and about 20° in a direction pointing towards the anterior plate of the first endplate and the plurality of anti-migration features of the second endplate may comprise a plurality of serrations that are oriented at an angle of about 15° and about 20° in a direction pointing towards the anterior plate of the second endplate. In various embodiments, a distance between the serrations may be about 0.15 cm and about 0.20 cm.

In other embodiments, the biocompatible cage may comprise a circular, an oval, or an elliptical cross-section. In various embodiments, the circular cross-section may comprise an inner diameter of about 0.55 cm and about 1.50 cm. In other embodiments, the oval or the elliptical cross-section may comprise an inner major diameter of about 1.15 cm and about 1.50 cm, and an inner minor diameter of about 0.45 cm and about 1.05 cm.

In various embodiments, the biocompatible cage may be about 1.3 cm and about 10 cm in length. In other embodiments, the plurality of apertures defining the mesh pattern may comprise circular, triangular, diamond, square rectangular, or hexagonal shape. In other embodiments, exposed surfaces of each of the cage holders may comprise openings configured to accommodate bone growth through the biocompatible cage and each of the first endplate and the second endplate, and the openings may comprise substantially the same size and type of shape as the apertures defining the mesh like pattern of the biocompatible cage.

In another aspect, a method for treating a plurality of vertebrae regions in a patient is disclosed, the method comprising: inserting a multi-level vertebral implant between an upper and lower vertebrae, wherein the multi-level vertebral implant may comprise; a biocompatible cage; and a first endplate and a second endplate that each comprise: (i) a bone contacting surface that is inclined with respect to a supporting surface disposed opposite from the bone contacting surface; (ii) a plurality of anti-migration features extending from each bone contacting surface and being configured to contact an adjacent vertebrae, respectively; (iii) a cage holder extending away from each support surface, each cage holder comprising a hollow protrusion defining a fusion aperture that extends through the bone contacting surface and supporting surface of each respective endplate; and (iv) an anterior plate extending orthogonally from each bone contacting surface and having at least one bone screw aperture configured to support a bone screw for anchoring into a ventral surface of a corresponding adjacent vertebrae; wherein the biocompatible cage comprises a body that extends in a longitudinal direction from a first end to a second end; and wherein the first end of the body is configured to couple to the cage holder of the first endplate and the second end of the body is configured to couple to the cage holder of the second endplate; attaching the first endplate of the multi-level vertebral implant to the upper vertebrae in a configuration that the bone contacting surface engages with an inferior surface and the anterior plate engages with a ventral surface of the upper vertebrae; positioning the biocompatible cage within a gap between the upper and the lower vertebrae; and attaching the second endplate of the multi-level vertebral implant to the lower vertebrae in a configuration that the bone contacting surface engages with a superior surface and the anterior plate engages with a ventral surface of the lower vertebrae. In other embodiments, method may comprise installing one or more bone screws through the one or more bone screw aperture on the anterior plate at an angle. In various embodiments, the method may comprise the biocompatible cage spanning more than one vertebral level.

In another aspect, a kit including a multi-level vertebral implant is disclosed herein, comprising: a biocompatible cage; and a first endplate and a second endplate that each comprise: (i) a bone contacting surface that is inclined with respect to a supporting surface disposed opposite from the bone contacting surface; (ii) a plurality of anti-migration features extending from each bone contacting surface and being configured to contact an adjacent vertebrae, respectively; (iii) a cage holder extending away from each support surface, each cage holder comprising a hollow protrusion defining a fusion aperture that extends through the bone contacting surface and supporting surface of each respective endplate; and (iv) an anterior plate extending orthogonally from each bone contacting surface and having at least one bone screw aperture configured to support a bone screw for anchoring into a ventral surface of a corresponding adjacent vertebrae; wherein the first and the second endplates comprise varying diameters and shapes of the fusion aperture; wherein the biocompatible cage comprises a body that extends in a longitudinal direction from a first end to a second end and has a hollow interior; wherein the biocompatible cage comprises varying lengths that is sufficient to span across one or more vertebral level; and wherein the first end of the body is configured to couple to the cage holder of the first endplate and the second end of the body is configured to couple to the cage holder of the second endplate. In various embodiments, the fusion aperture of the kit may comprise a circular, an oval, or an elliptical shape and the fusion aperture communicates with the hollow interior of the biocompatible cage to facilitate boney ingrowth and spinal fusion. In other embodiments, the biocompatible cage of the kit may comprise a circular, an oval, or an elliptical cross-section.

The details of one or more aspects of the disclosure are set forth in the accompanying drawings and the description below. Other features, objects, and advantages of the techniques described in this disclosure will be apparent from the description and drawings, and from the claims.

DETAILED DESCRIPTION

Figure 1:
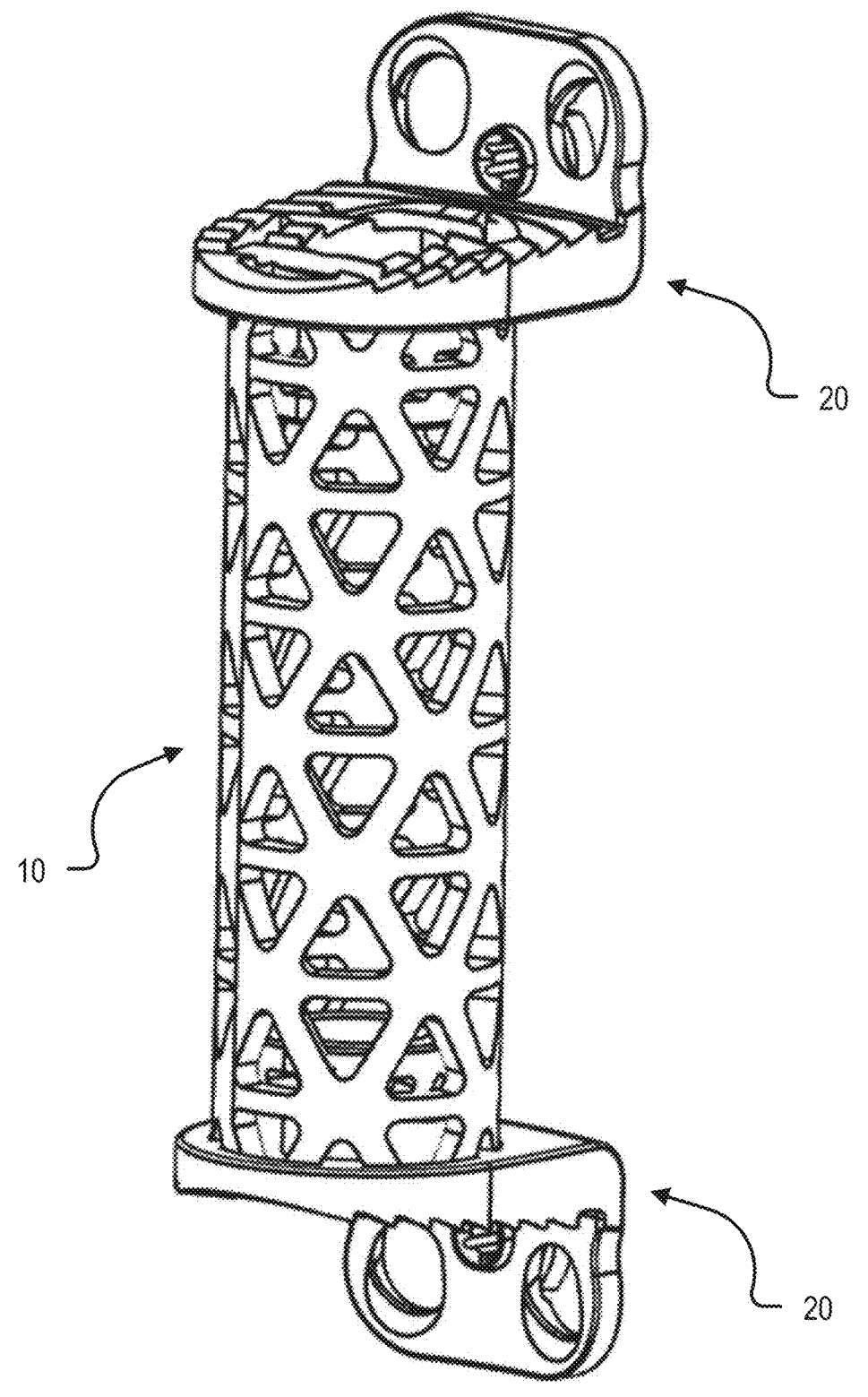
FIG. 1 is a perspective view of a multi-level vertebral implant of the present disclosure.

Embodiments of the present disclosure relate generally, for example, to spinal stabilization systems, and more particularly, to implants used as spinal stabilization systems. Embodiments of the devices and methods are described below with reference to the Figures.

The following discussion omits or only briefly describes certain components, features and functionality related to medical implants, installation tools, and associated surgical techniques, which are apparent to those of ordinary skill in the art. It is noted that various embodiments are described in detail with reference to the drawings, in which like reference numerals represent like parts and assemblies throughout the several views, where possible. Reference to various embodiments does not limit the scope of the claims appended hereto because the embodiments are examples of the inventive concepts described herein. Additionally, any example(s) set forth in this specification are intended to be non-limiting and set forth some of the many possible embodiments applicable to the appended claims. Further, particular features described herein can be used in combination with other described features in each of the various possible combinations and permutations unless the context or other statements clearly indicate otherwise.

Terms such as "same," "equal," "planar," "coplanar," "parallel," "perpendicular," etc. as used herein are intended to encompass a meaning of exactly the same while also including variations that may occur, for example, due to manufacturing processes. The term "substantially" may be used herein to emphasize this meaning, particularly when the described embodiment has the same or nearly the same functionality or characteristic, unless the context or other statements clearly indicate otherwise. Additionally, it shall be understood that the term "about" encompasses a variation of at least +/−10% from the example values provided herein.

The following discussion includes a description of a multi-level vertebral implant and related methods of manufacturing the multi-level vertebral implant in accordance with the principles of the present disclosure. Alternate embodiments are also disclosed. Reference is made in detail to the exemplary embodiments of the present disclosure, which are illustrated in the accompanying figures. FIGS. 1-13, illustrate various components of a multi-level vertebral implant, such as, for example, a multi-level vertebral implant having endplates 20, 30, 40, or 50.

Various embodiments and components of the multi-level vertebral implant of the present disclosure may be fabricated from biologically acceptable materials suitable for medical applications, including metals, synthetic polymers, ceramics, and bone material and/or their composites. For example, the components, individually or collectively, can be fabricated from materials such as stainless steel alloys, commercially pure titanium, titanium alloys, Grade 5 titanium, super-elastic titanium alloys, cobalt-chrome alloys, super-elastic metallic alloys (e.g., Nitinol, super elasto-plastic metals, such as GUM METAL®), ceramics and composites thereof such as calcium phosphate (e.g., SKELITE™), thermoplastics such as polyaryletherketone (PAEK) including polyetheretherketone (PEEK), polyetherketoneketone (PEKK) and polyetherketone (PEK), carbon-PEEK composites, PEEK-BaSO$_4$ polymeric rubbers, polyethylene terephthalate (PET), fabric, silicone, polyurethane, silicone-polyurethane copolymers, polymeric rubbers, polyolefin rubbers, hydrogels, semi-rigid and rigid materials, elastomers, rubbers, thermoplastic elastomers, thermoset elastomers, elastomeric composites, rigid polymers including polyphenylene, polyamide, polyimide, polyetherimide, polyethylene, epoxy, bone material including autograft, allograft, xenograft or transgenic cortical and/or corticocancellous bone, and tissue growth or differentiation factors, partially resorbable materials, such as, for example, composites of metals and calcium-based ceramics, composites of PEEK and calcium based ceramics, composites of PEEK with resorbable polymers, totally resorbable materials, such as, for example, calcium based ceramics such as calcium phosphate, tri-calcium phosphate (TCP), hydroxyapatite (HA)-TCP, calcium sulfate, or other resorbable polymers such as polyketide, polyglycolide, polytyrosine carbonate, polycaprolactone, polylactic acid or polylactide and their combinations.

Figure 2:
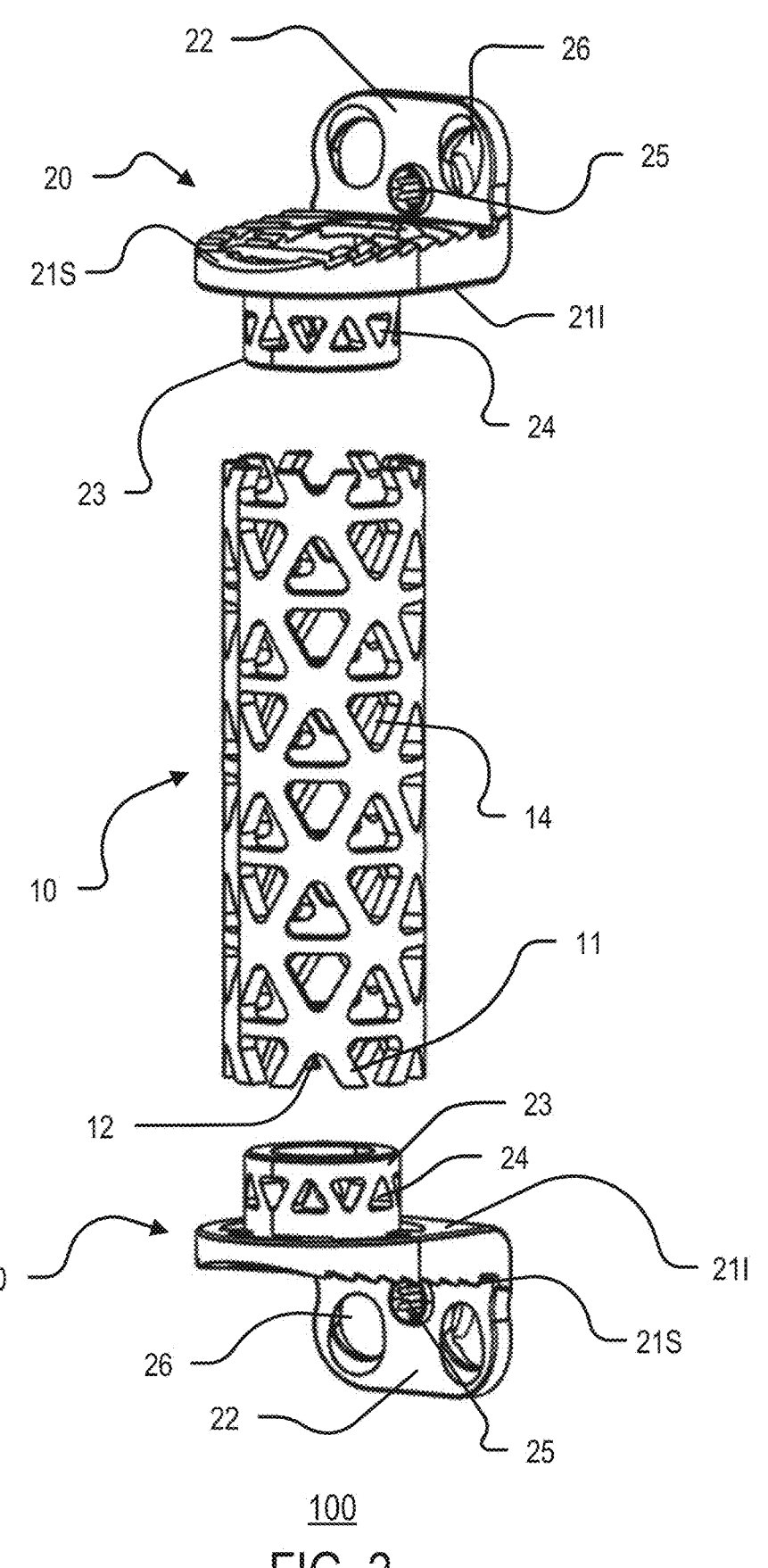
FIG. 2 is an exploded parts view of a multi-level vertebral implant.
Figure 3:
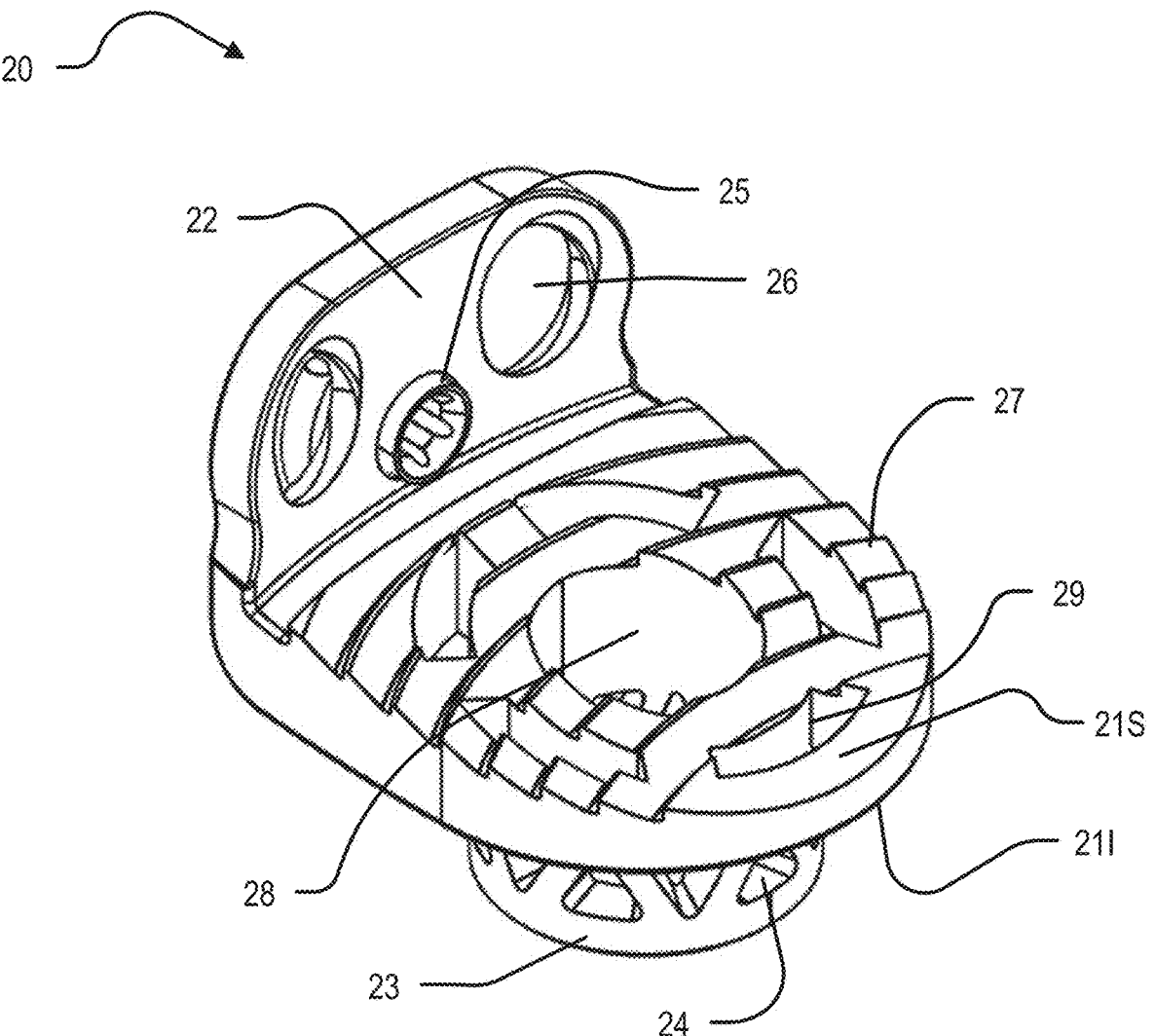
FIG. 3 is a front perspective view of an embodiment of an endplate.
Figure 4:
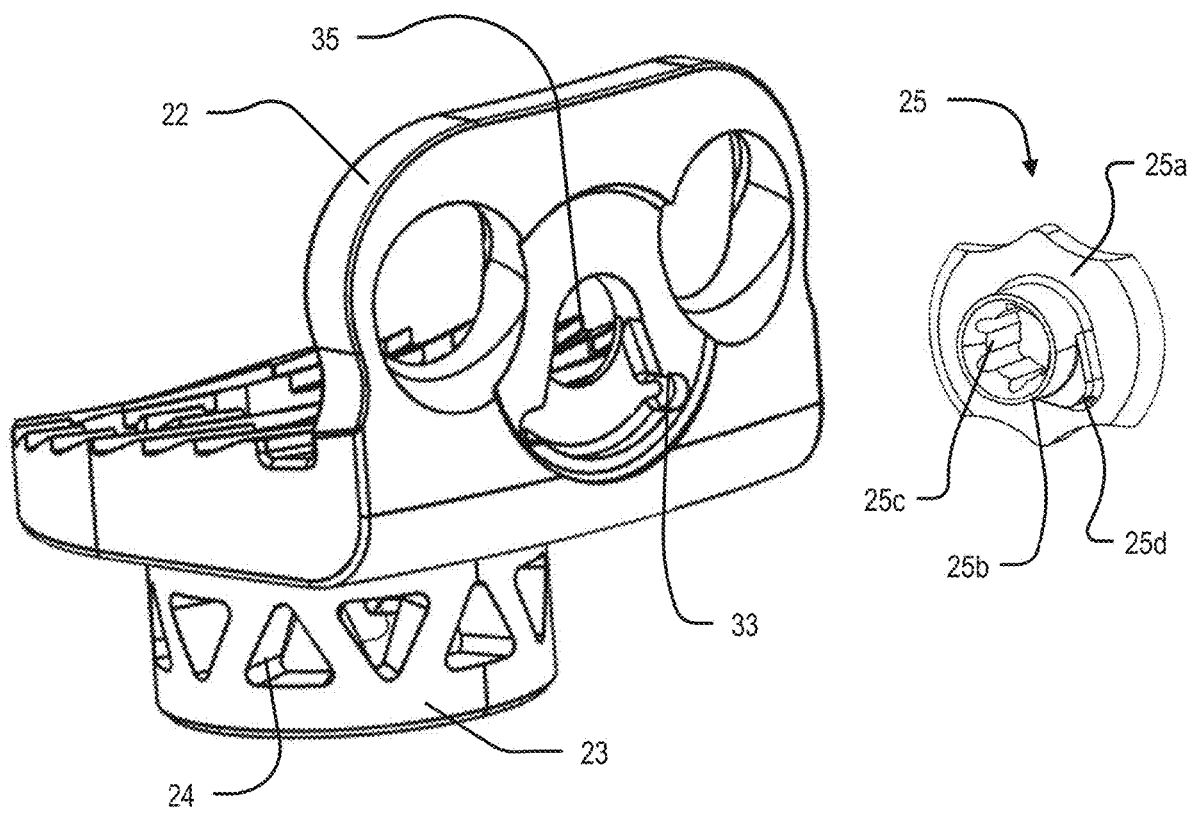
FIG. 4 is a rear perspective view of an embodiment of an endplate.
Figure 5:
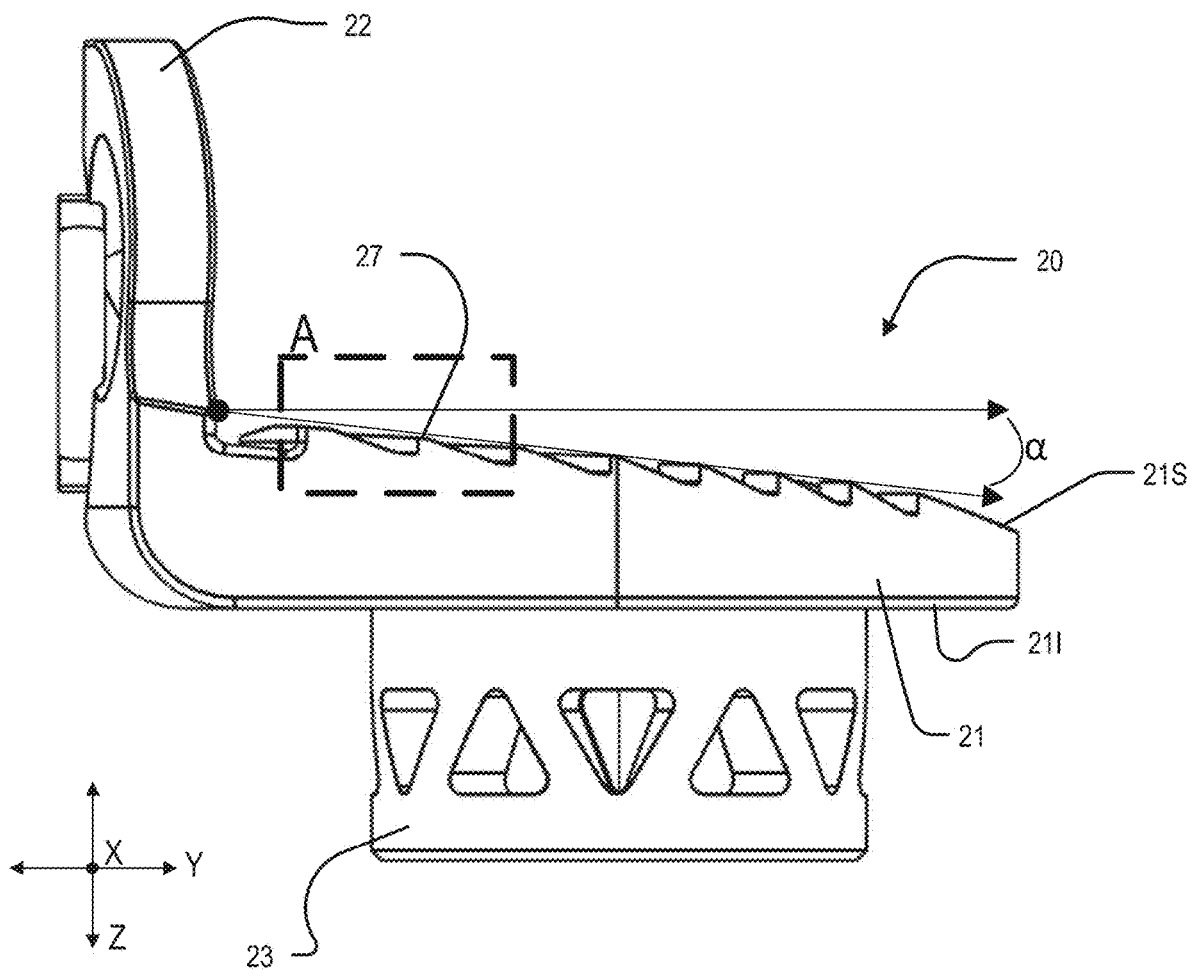
FIG. 5 is a side perspective view of an embodiment of an endplate.
Figure 6:
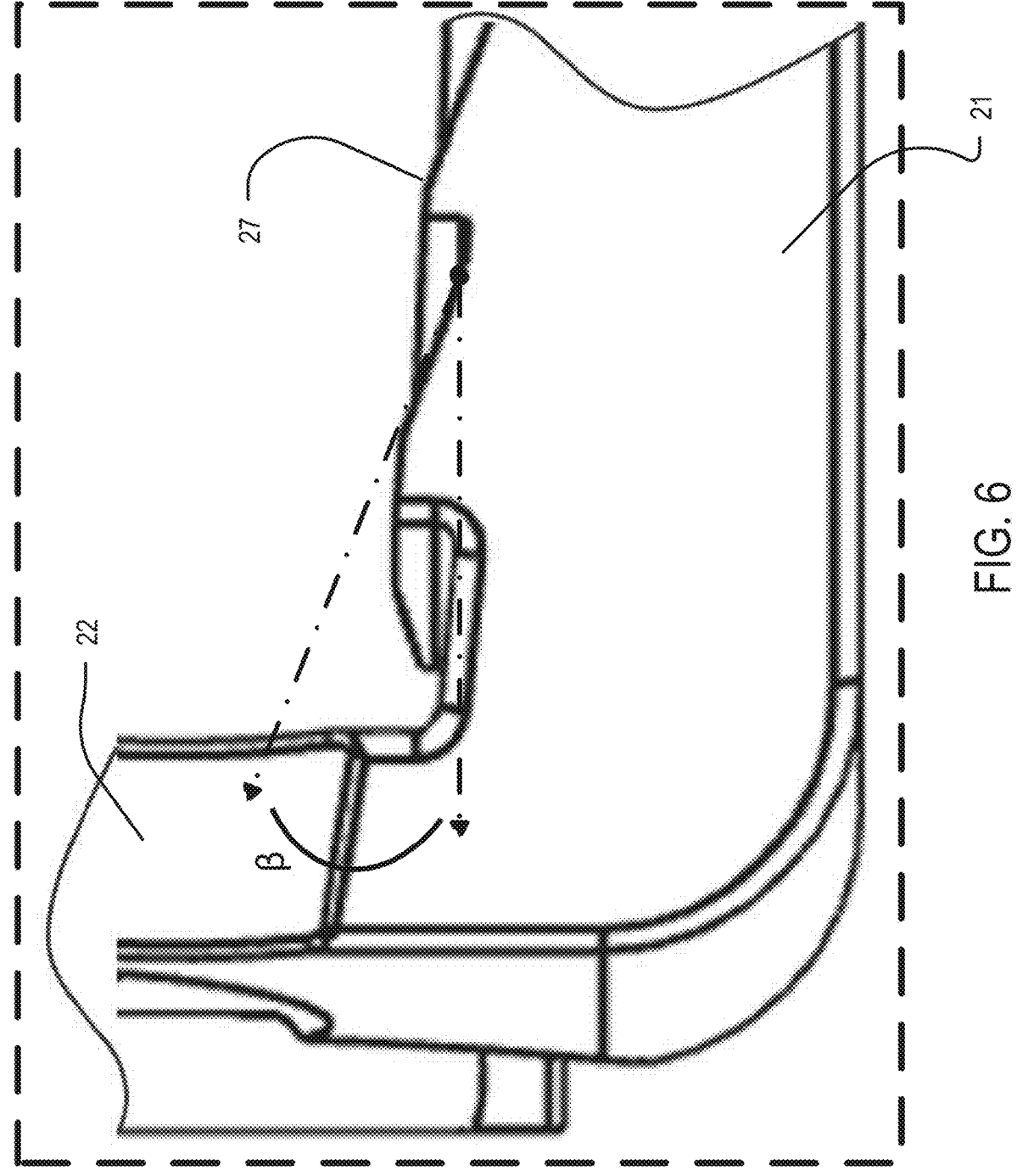
FIG. 6 is a zoomed in perspective view of serrations of an endplate in FIG. 5.
Figure 7:
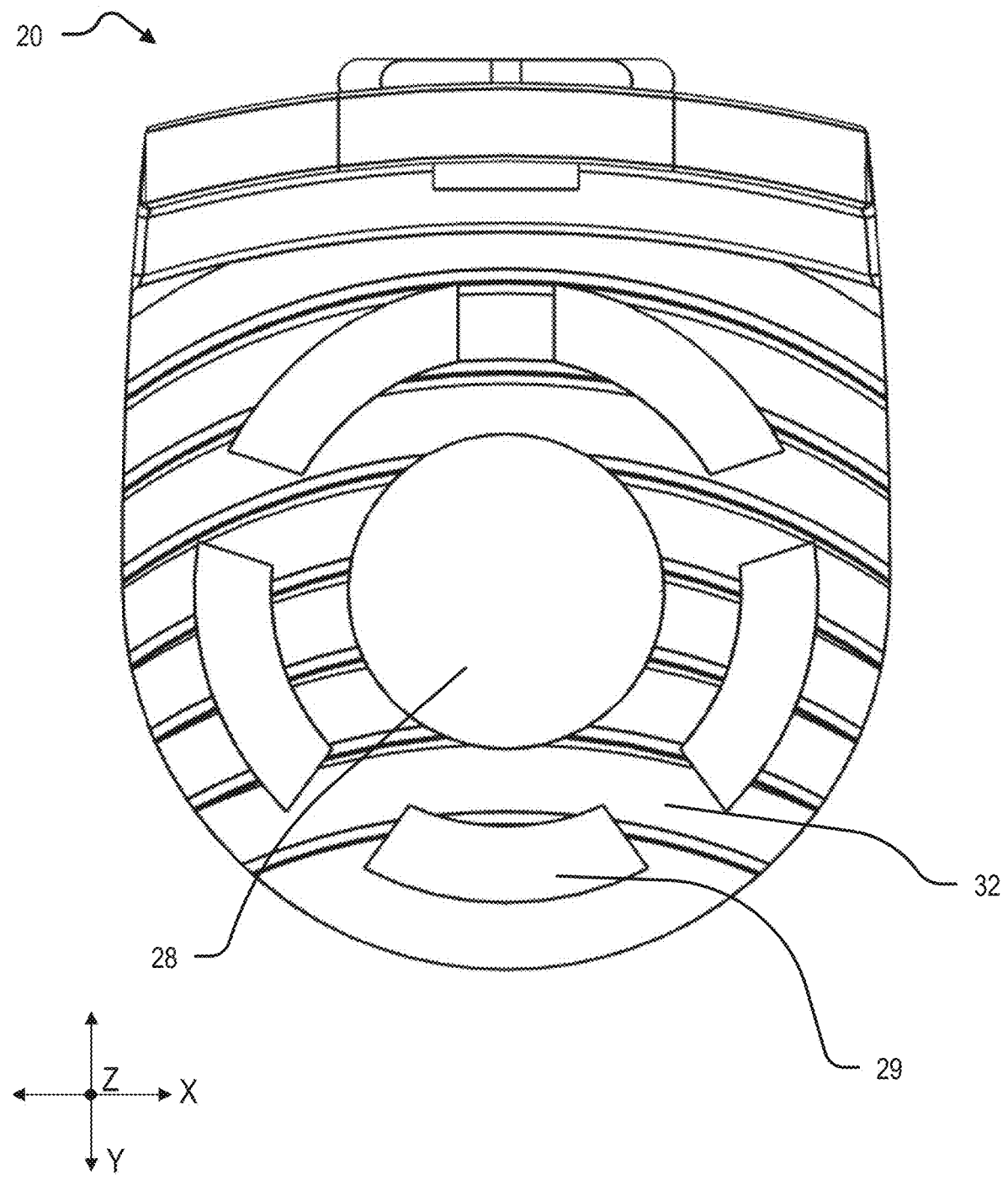
FIG. 7 is a top-down perspective view of an embodiment of an endplate.
Figure 8:
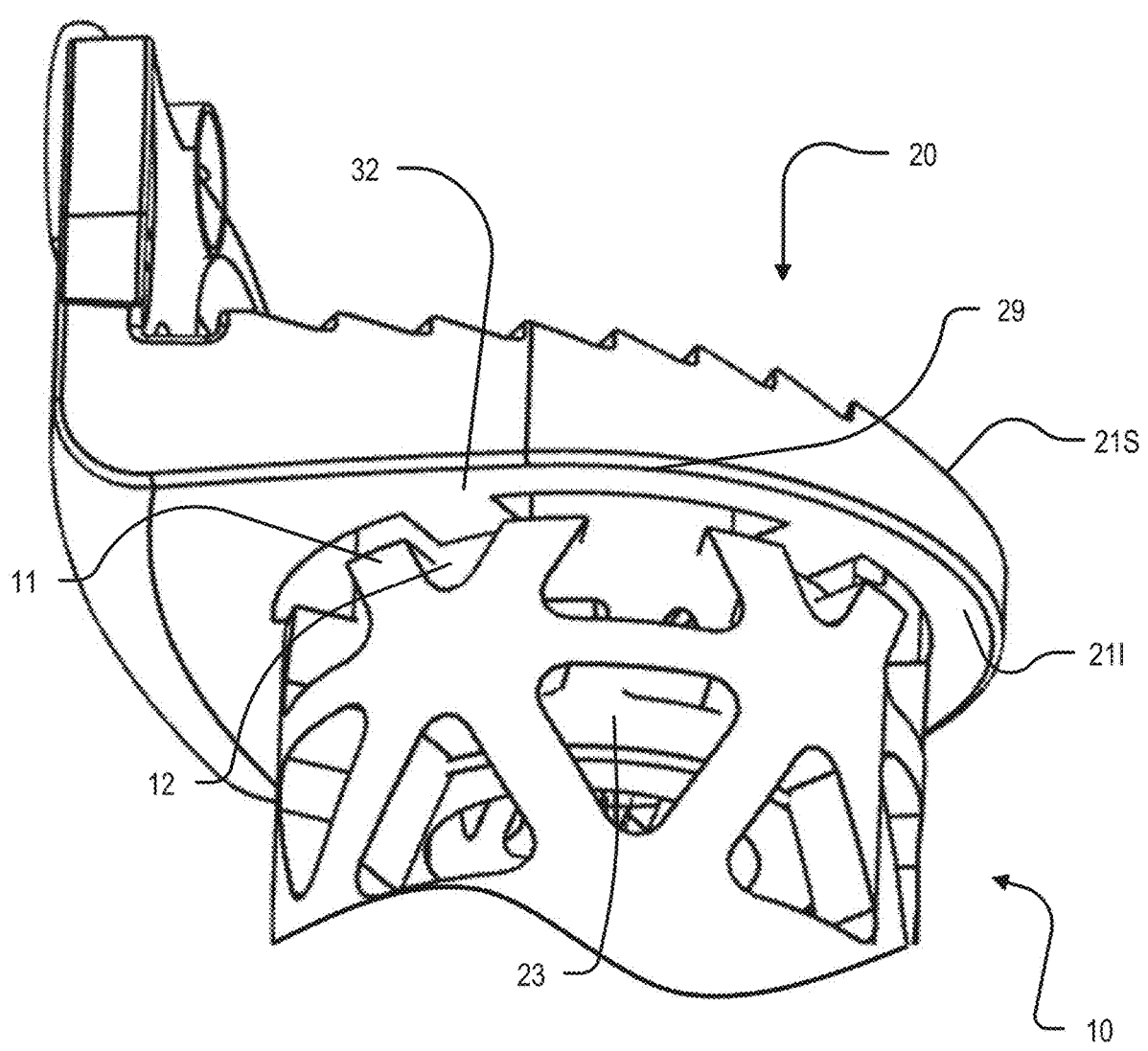
FIG. 8 is a lower perspective view of an embodiment of an endplate.
Figure 9:
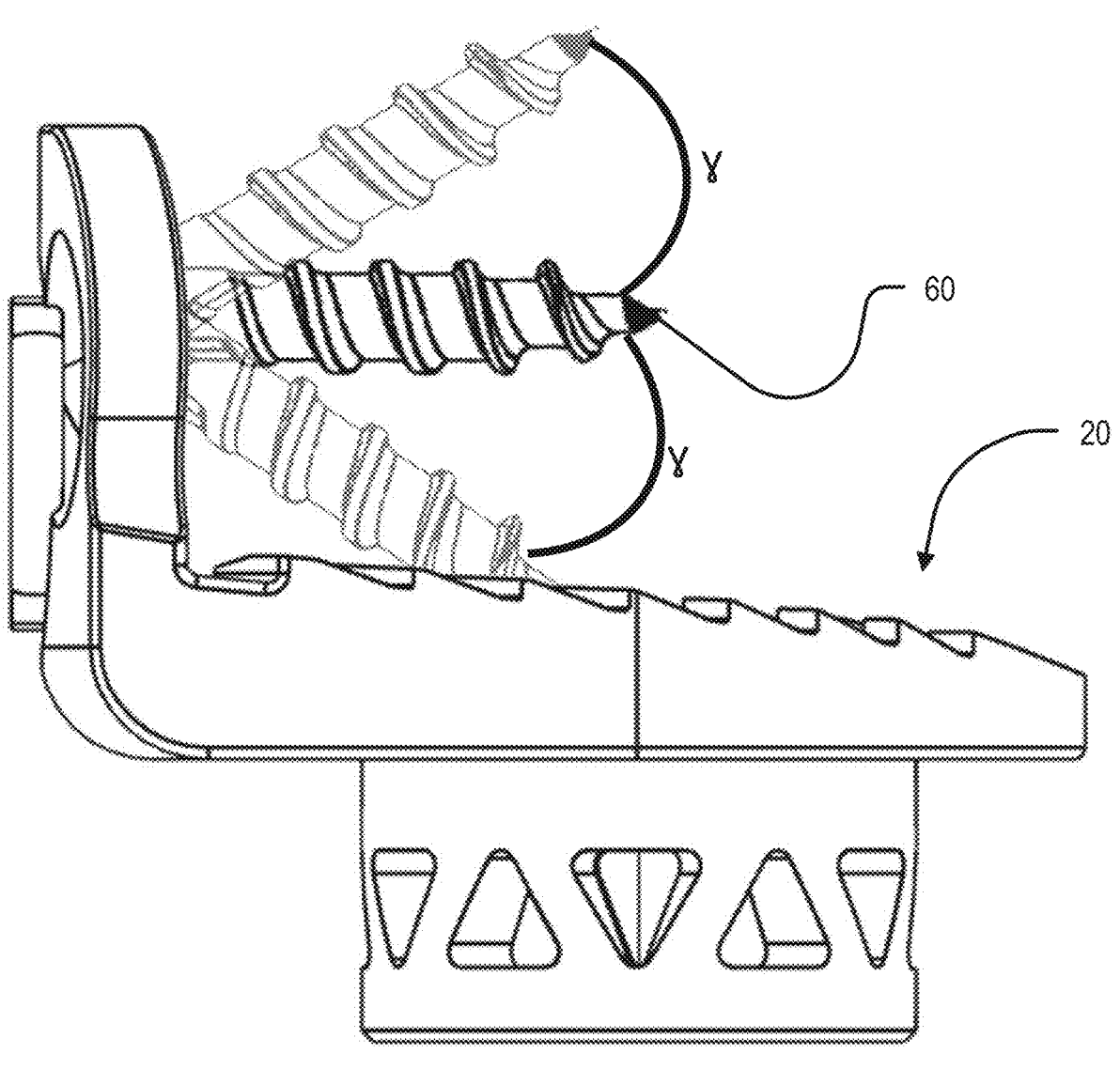
FIG. 9 is a side perspective view of an embodiment of an endplate showing a bone screw projection.
Figure 10:
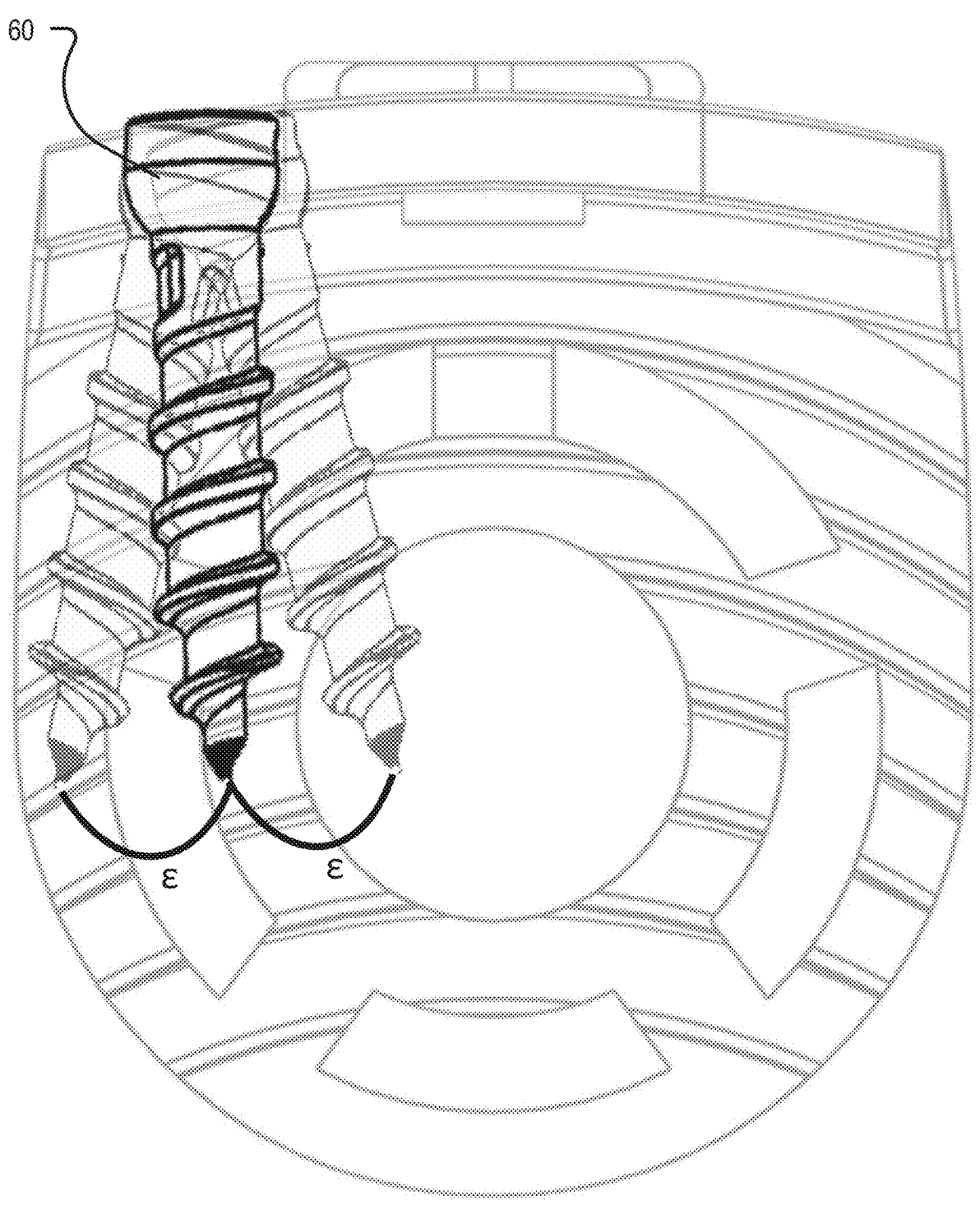
FIG. 10 is a top-down perspective view of an embodiment of an endplate showing a bone screw projection.
Figure 11:
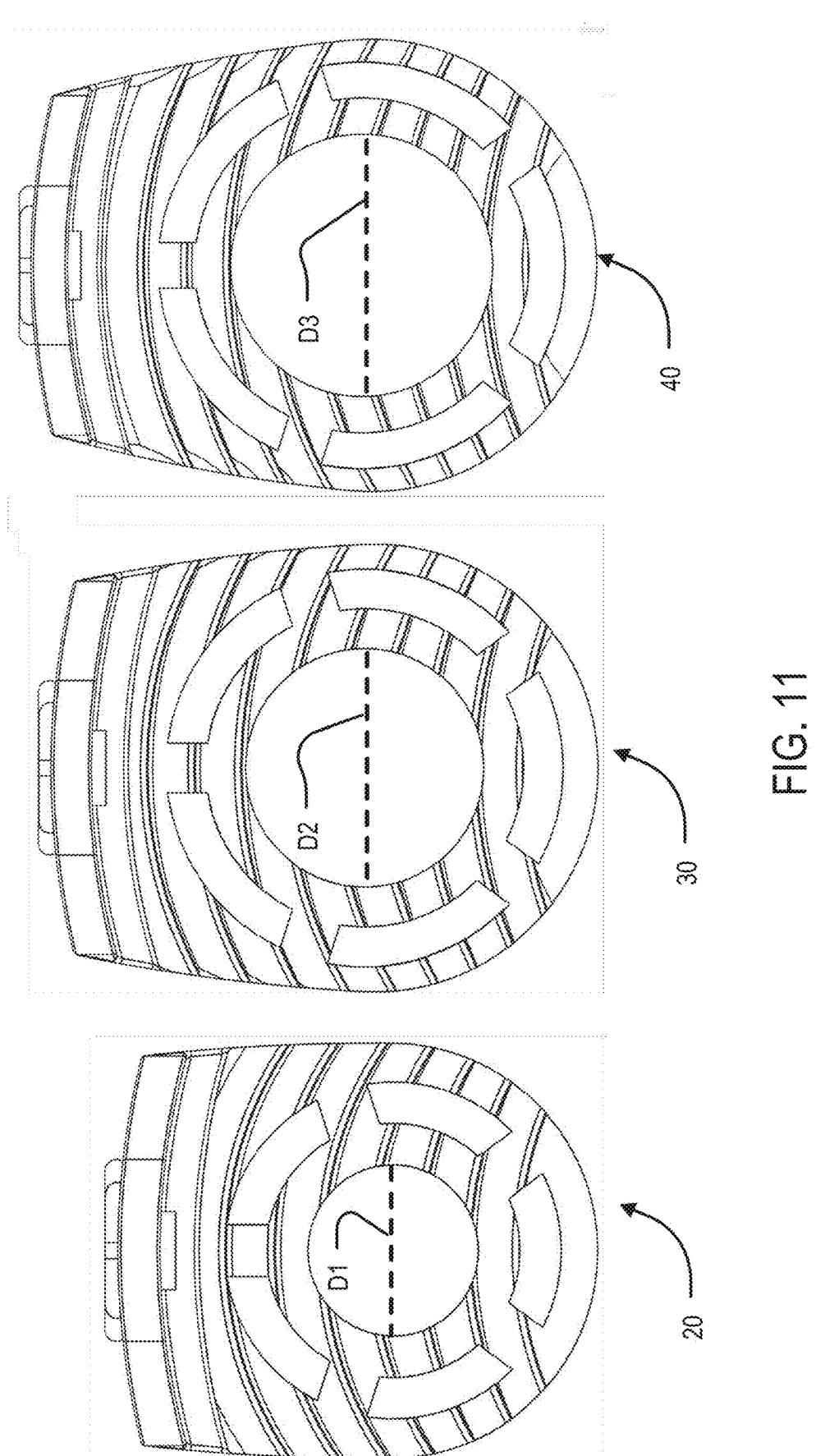
FIG. 11 is a top-down perspective view of various size endplates.
Figure 12:
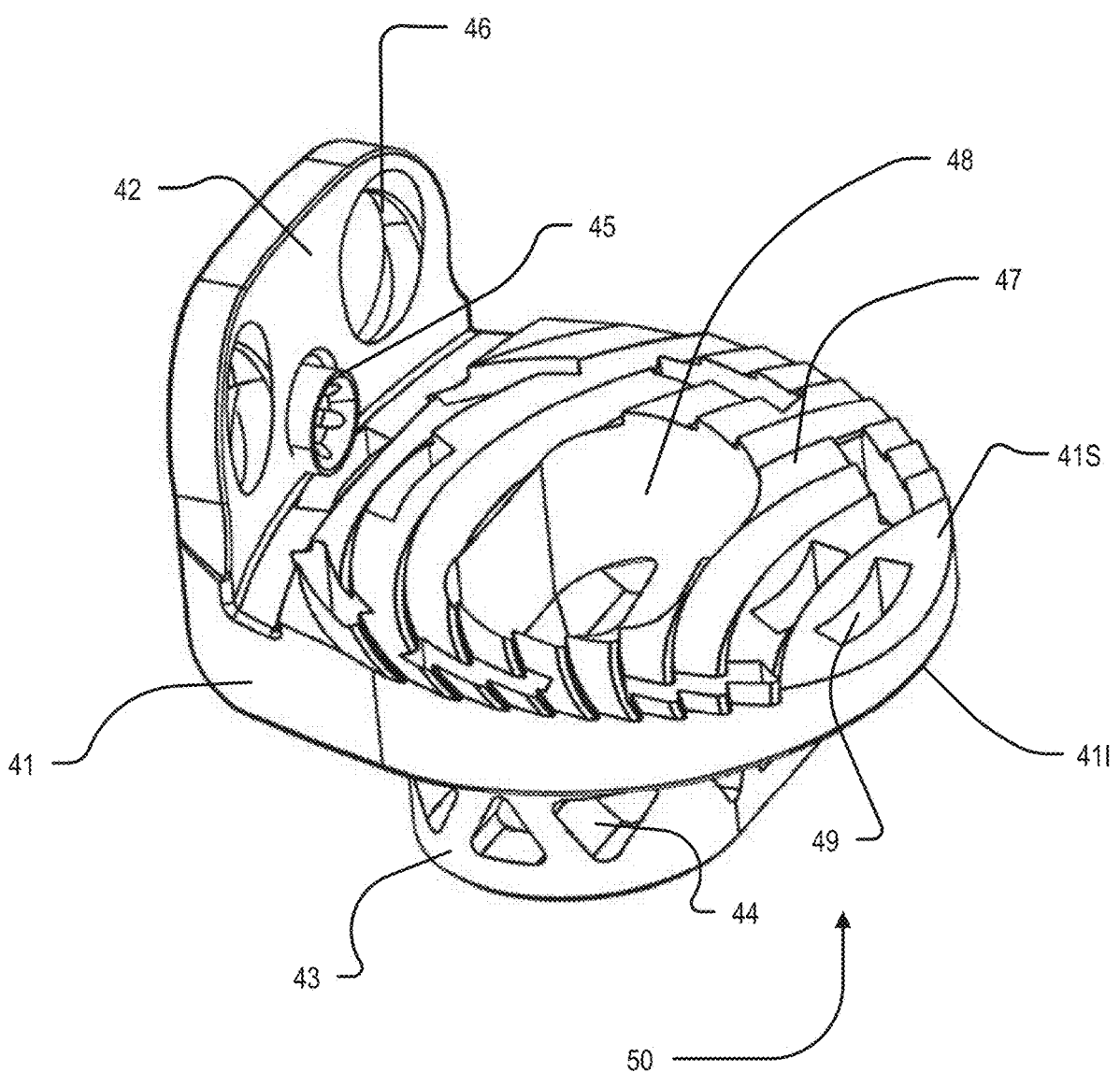
FIG. 12 is a front perspective view of another embodiment of an endplate.
Figure 13:
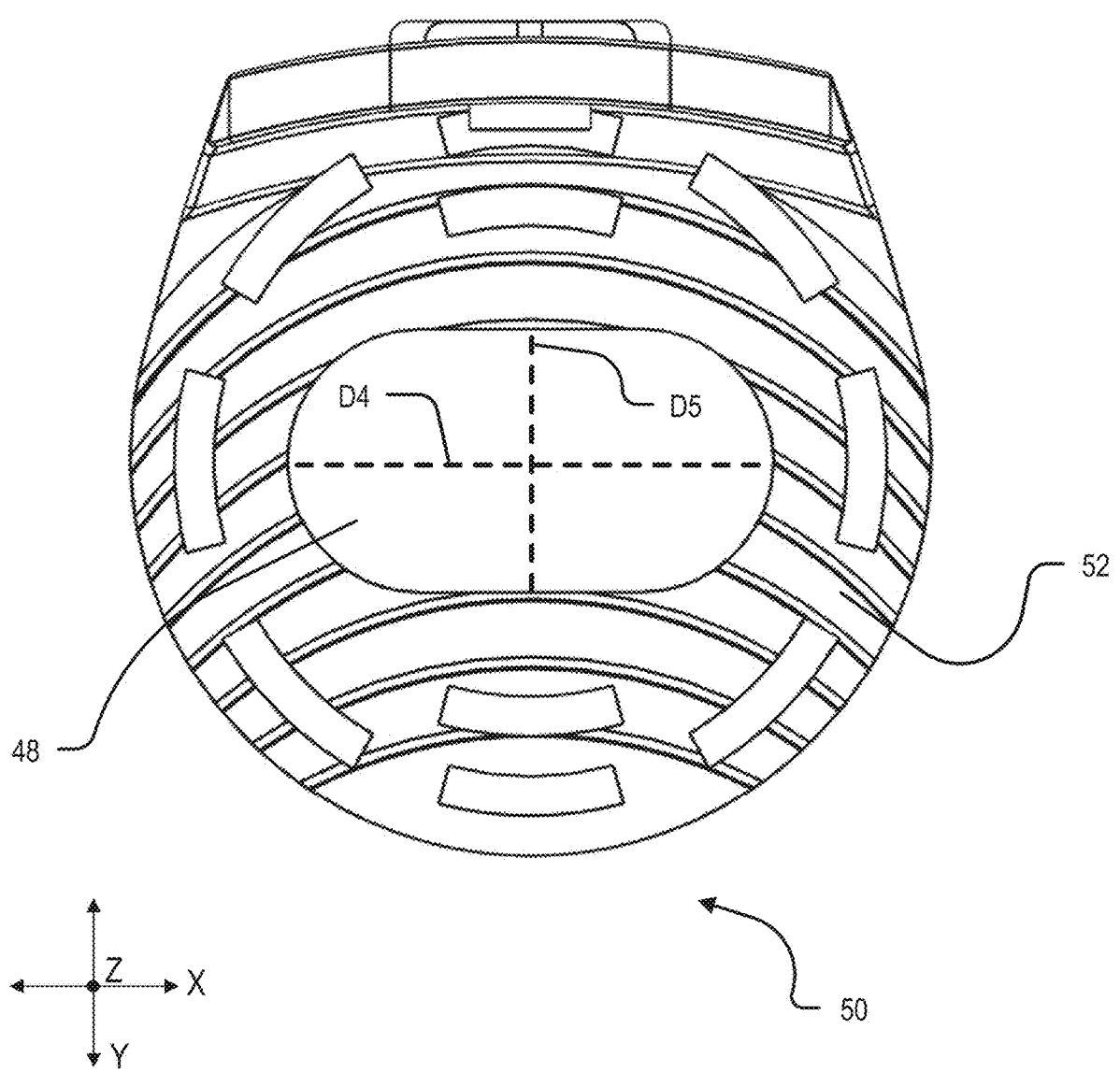
FIG. 13 is a top-down perspective view of a second example of an endplate.
Figure 14:
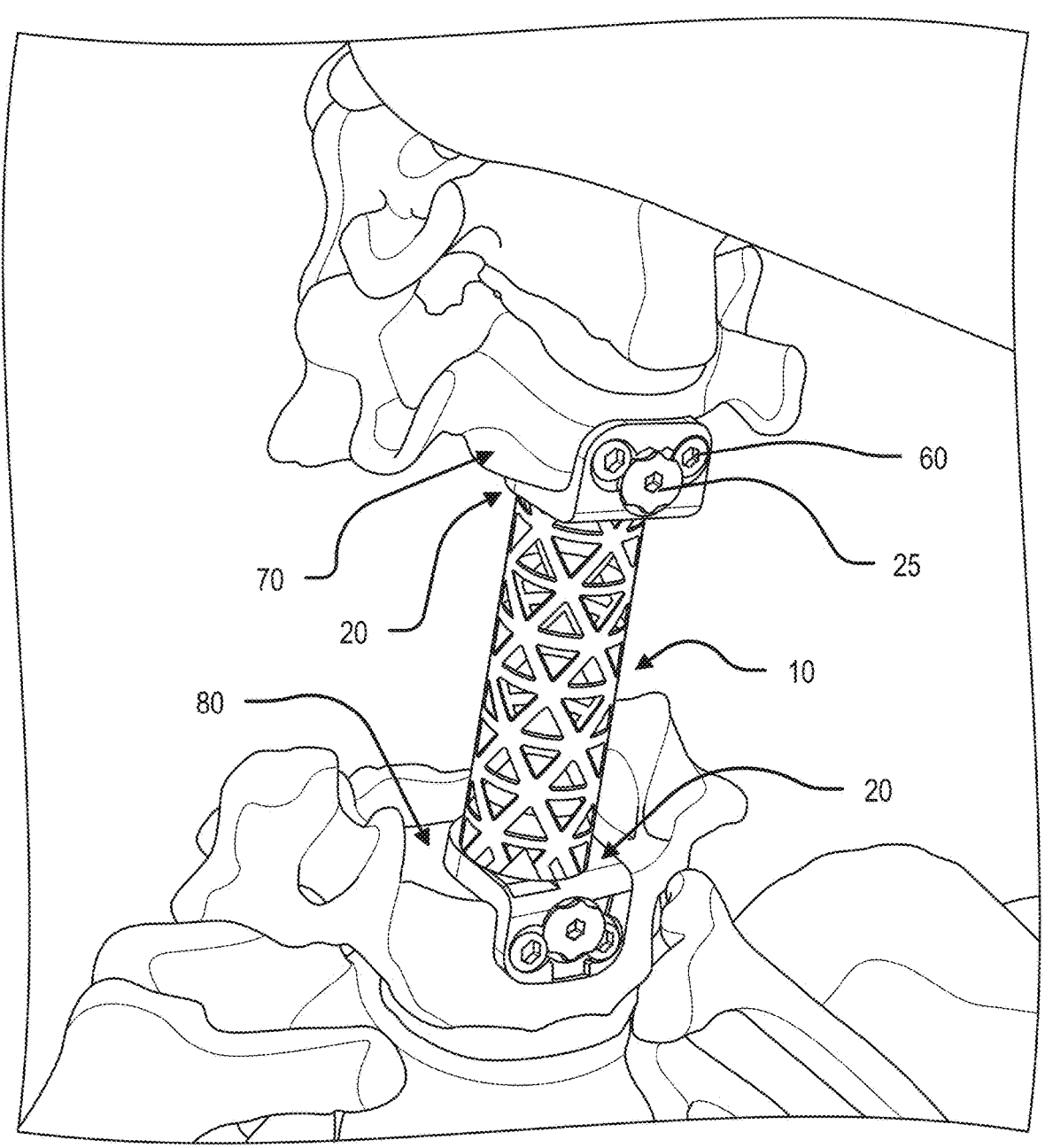
FIG. 14 depicts a multi-level vertebral implant in an installed state.

Referring generally to FIGS. 1-2, a multi-level vertebral implant of the present disclosure is shown. FIGS. 3-8 illustrate various views of endplate 20. Referring generally to FIGS. 3 and 4, front and rear perspective views of endplate 20 are shown. FIGS. 5 and 6 each illustrate a side perspective view of endplate 20; and FIGS. 7 and 8 illustrate top-down and bottom-up views of endplate 20. FIGS. 9 and 10 illustrate the projected path of bone screw installation. FIG. 11 illustrates endplates 20, 30, and 40 having various sizes. FIGS. 12 and 13 illustrate another endplate embodiment for use with differently shaped biocompatible cages, or pyramesh cages. FIG. 14 illustrates a multi-level vertebral implant in an installed state.

In FIG. 1, a multi-level vertebral implant assembly, according to an embodiment of the present disclosure, is disclosed. A multi-level implant 100 may comprise biocompatible cage 10 disposed between two endplates 20. FIG. 2 is an exploded perspective view showing biocompatible cage 10 disposed between two endplates 20 at the cage ends. Biocompatible cage 10 may comprise a generally tubular body extending in a longitudinal direction and may have a hollow interior configured to receive cage holder 23 of endplate 20 at each end of biocompatible cage 10. In various embodiments, cage holder 23 may have a length of about 0.5 cm and about 1.2 cm, about 0.5 cm and about 0.75 cm, about 0.75 cm and about 1.0 cm, or about 1.0 cm and about 1.2 cm, such that when cage holder 23 is disposed in the hollow interior of biocompatible cage 10, the movement of biocompatible cage 10 is constrained. Biocompatible cage 10 may further comprise a plurality of protrusions 11 at the ends and may form a groove 12 that may interact with features of endplate 20 for stabilizing and preventing movement of endplate 20 in an assembled configuration, as further discussed below. In various embodiments, the cross-sections of biocompatible cage 10 may generally have a circular, oval, or elliptical cross-section. In various embodiments, biocompatible cage 10 may have a circular cross-section between about 0.55 cm and about 1.50 cm, and may encompass any values within this range such as, for example, between about 0.55 cm and about 0.75 cm, about 0.75 cm and about 1.00 cm, about 1.00 cm and about 1.25 cm, or about 1.25 cm and about 1.50 cm inner diameter. In some embodiments, biocompatible cage 10 having an oval or an elliptical cross-section may have a major inner diameter of about 1.15 cm and about 1.50 cm, about 1.15 cm and about 1.30 cm, or about 1.30 cm and about 1.50 cm. In various embodiments, biocompatible cage 10 having an oval or an elliptical cross-section may have a minor inner diameter of about 0.45 cm and about 1.05 cm, about 0.45 cm and about 0.75 cm, or about 0.75 cm and about 1.05 cm. In various embodiments, biocompatible cage 10 may have a length between about 1.3 cm and about 10 cm, and may encompass any values within this range such as, for example, about 1.3 cm and about 3 cm, about 3 cm and about 6 cm, about 6 cm and about 8 cm, or about 8 cm to about 10 cm, to support a distance sufficient to span at least two vertebral levels for performing surgical procedures such as corpectomy. In various embodiments, biocompatible cage 10 may include a mesh (or mesh like body) comprising a plurality of apertures 14 extending through a sidewall of the body that are configured to accept osteogenic material, bone graft, or other bone growth and healing substances to facilitate bone growth. In various embodiments, the mesh may comprise polygonal shape openings, including, for example, generally circular, triangular, diamond, square, rectangular, or hexagonal shapes.

In various embodiments, multi-level vertebral implant 100 may comprise one or more endplate(s) 20. Generally referring to FIGS. 3 and 4, the front and rear perspectives of endplate 20 are disclosed. In some embodiments, endplate 20 may comprise vertebral endcap 21 which may be configured for contacting the bone surface of a vertebra at an incline with respect to a supporting surface 211 of the vertebral endcap 21 disposed opposite from bone contacting surface 21S of the vertebral endcap 21. This inclined surface may facilitate aligning an angle of respective vertebra (and/or vertebral column) in a proper orientation. In various embodiments, vertebral endcap 21 may comprise a plurality of anti-migration features such as serrations 27 extending from surface of each bone contacting surface 21S that are configured to optimize the contact to surface of the adjacent vertebrae. In this configuration, subsidence between serrations 27 and the adjacent vertebrae is optimized reducing migration of endplate 20 from the adjacent vertebrae. In some embodiments, endplate 20 may comprise cage holder 23 extending away from each support surface and may comprise a hollow protrusion defining a fusion aperture 28 that extends through bone contacting surface 21S and supporting surface 211 of each respective endplate 20. In various embodiments, cage holder 23 may have generally the same shape as fusion aperture 28. In various embodiments, the diameter of fusion aperture 28 and the inner diameter of the adjacent corresponding cage holder 23 may be the same such that a centerpoint of each fusion aperture 28 and a centerpoint of the adjacent corresponding cage holder may be co-axially aligned. In various embodiments, the endplate 20 may comprise a plurality of anti-rotation slots 29 disposed around each corresponding cage holder 23 and extending through the bone contacting surface 21S and supporting surface 211 of each respective endplate 20.

In various embodiments, cage holder 23 may comprise a plurality of cage openings 24 on exposed surfaces thereof that are configured to accept osteogenic material, bone graft, or other bone growth and healing substances to accommodate and facilitate bone growth through biocompatible cage 10 and each of the first and the second endplates 20. In various embodiments, cage opening 24 may comprise various polygonal shape openings, including generally triangular, rectangular, diamond, circular, or hexagonal shapes. In some embodiments, cage opening 24 may have a generally similar, substantially similar, or the same shape type as mesh aperture 14 of biocompatible cage 10.

In various embodiments, endplate 20 may comprise anterior plate 22 extending orthogonally from each bone contacting surface 21S of endplate 20. In some embodiments, anterior plate 22 may be configured at an angle, for example, in a concave shape to provide optimal contact with the curvature of a ventral surface of corresponding adjacent vertebrae. In various embodiments, the inner surface of anterior plate 22 may be angled in a range of about 0° and about 6°. In various embodiments, anterior plate 22 may comprise one or more bone screw holes or apertures 26 configured to support a bone screw 60 (as first shown in FIG. 9) for anchoring into the ventral surface of a corresponding adjacent vertebrae at various angles. In some embodiments, anterior plate 22 may comprise a locking mechanism configured to keep a corresponding bone screw 60 from backing out. In various embodiments, the locking mechanism may include locking cap 25, locking groove 33, and locking slot 35.

As illustrated in FIG. 4, locking cap 25 may comprise a plate 25a, cylinder 25b extending longitudinally from plate 25a, core 25c extending through cylinder 25b configured to be inserted into the aperture of the locking slot 35, and plate 25a for receiving an inserter tool (not shown), and notch 25d configured to be disposed in locking groove 33. In various embodiments, cylinder 25b may be configured to be inserted into locking slot aperture 35 on anterior plate 22. In various embodiments, locking cap 25 may be rotated by an inserter tool engaged with core 25c. In various embodiments, core 25c may comprise a shape that when the inserter tool is rotated about longitudinal axis of cylinder 25b, core 25c provides a resistive force that displaces notch 25b from locking groove 33 to freely rotate locking cap 25 between locked and unlocked positions. In various embodiments, core 25c may take a hexalobular shape, although other shapes such as hexagonal, polygonal, Torx, X-shape, plus sign-shape, tri-wing, etc. may also be contemplated. In various embodiments, after insertion of bone screw 60 in bone screw hole 26, cylinder 25b of locking cap 25 may be inserted through locking slot aperture 35 and rotated about the longitudinal axis of cylinder 25b such that notch 25d is disposed in locking groove 33. In this configuration, plate 25a covers bone screw hole 26, preventing access to bone screw 60 as well as preventing bone screw 60 from backing out post installation.

Now referring to FIGS. 5 and 6, side-perspective views of endplate 20 are shown. In various embodiments, bone contacting surface 21S of endplate 20 may be inclined at an angle as defined by a between about 0° and about 6° to provide optimal engagement of endplate 20 with adjacent vertebrae and to provide a patient specific lordotic angle for maintaining the curvature of the spine. As shown in FIG. 6, endplate 20 may comprise a plurality of serrations 27 in a direction pointing towards anterior endplate 22 at an angle defined by β to promote optimal subsidence of vertebral endcap 21 to the vertebrae and prevent migration of the implant 100 post-insertion. In various embodiments, features of the first endplate 20 comprise a plurality of serrations 27 that are oriented at an angle of about 15° and about 20° in a direction pointing towards the anterior plate 22 of the first endplate 20 and the plurality of anti-migration features of the second endplate 20 comprise a plurality of serrations 27 that are oriented at an angle of about 15° and about 20° in a direction pointing towards the anterior plate 22 of the second endplate 20. In some embodiments, the distance between serrations 27 of both the first and second endplates 20 may be about 0.15 cm and about 0.20 cm.

FIGS. 7 and 8 illustrate a top-down perspective and bottom-up perspective of endplate 20 showing fusion aperture 28 and anti-rotation slot 29. In various embodiments, fusion aperture 28 may be configured to accept osteogenic material, bone graft, or other bone growth and healing substances to facilitate bone growth. In various embodiments, fusion aperture 28 may comprise a circular, oval, or elliptical shape or cross-section. In various embodiments, the diameter of fusion aperture 28 generally having a circular cross-section may be about 0.25 cm and about 0.40 cm, and may encompass any values within this range such as, for example, about 0.25 cm and about 0.30 cm, about 0.30 and about 0.35 cm, or about 0.35 and about 0.40 cm diameter. In some embodiments, fusion aperture 28 having an oval or an elliptical cross-section may have a major diameter of about 0.90 cm and about 1.10 cm, about 0.90 and about 0.95 cm, about 0.95 cm and about 1.00 cm, about 1.00 cm and about 1.05 cm, or about 1.05 cm and about 1.10 cm. In various embodiments, fusion aperture 28 having an oval or an elliptical cross-section may have a minor diameter of about 0.55 cm and about 0.70 cm, about 0.55 cm and about 0.60 cm, about 0.60 cm and about 0.65 cm, or about 0.65 cm and about 0.70 cm.

In various embodiments, endplate 20 may comprise about 4 and 6 anti-rotation slots 29. In various embodiments, as shown in FIGS. 7 and 8, a plurality of anti-rotation slot 29 may be generally oriented in a periodic configuration such that there are solid gaps 32 between anti-rotation slots 29 to engage with the general shape of the ends of biocompatible cage 10. As shown in FIG. 8, protrusions 11 at the end of biocompatible cage 10 may be configured to engage with anti-rotation slot 29 in a manner such that grooves 12 at the cage ends engage with solid gap 32, stabilizing endplate 20 and biocompatible cage 10 in place. In this configuration, cage holder 23 may be disposed in the hollow interior of biocompatible cage 10 such that it constrains the movement of biocompatible cage 10 in an installed configuration. In various embodiments, cage holder 23 may extend into the hollow interior of biocompatible cage 10 and may have a length of about 0.5 cm and about 1.20, about 0.5 cm and about 0.75 cm, about 0.75 cm and about 1.0 cm, or about 1.0 cm and about 1.20 cm to constrain and suppress both the radial and axial movements of biocompatible cage 10 in an installed configuration.

Now referring to FIGS. 9 and 10, the installation of bone screw 60 through anterior plate 22 for fixation to a corresponding vertebral surface is disclosed. As disclosed above, bone screw hole 26 may be configured to guide one or more bone screw 60 at an angle along both sagittal (vertical movements in cranial and caudal directions) and transverse (horizontal movement in a lateral direction) planes to provide optimal projection path for bone screw 60 to be installed on the ventral surface of the adjacent vertebrae. This configuration may thereby be useful for maximizing contact between anterior plate 22 of first and second endplates 20 with and the adjacent vertebrae an installed state. As shown in FIG. 9, in various embodiments, bone screw 60 may be inserted with angulation ty of about 0° to 40° along the sagittal plane in both upper (cranial) and lower (caudal) projections, i.e., −40° to 40° total displacement, wherein straight insertion, i.e., solid bone screw 60 in FIG. 9, corresponds to an insertion angle of 0°. In various embodiments, as shown in FIG. 10, bone screw 60 may be inserted with angulation & of about +0° to 20° along the transverse plane in both lateral directions projections, i.e., −20° to 20° total displacement, wherein straight insertion, i.e., solid bone screw 60 in FIG. 10, corresponds to an insertion angle of 0°.

FIG. 11 illustrates various size endplates 20, 30, and 40, with varying diameters D1, D2, and D3, for use with various size biocompatible cages 10, e.g., various diameter, round pyramesh cages. Now referring to FIGS. 12 and 13, front and top-down perspective views of a second example of an endplate 50 for use with biocompatible cage 10 having a generally an oval shape, e.g., ovoid pyramesh cage, is disclosed. In various embodiments, endplate 50 may have the same, similar and/or substantially the same features and functionality as explained above with respect to endplate 20. For example, endplate 50 may include, but is not limited to, features such as vertebral endcap 41, anterior plate 42, cage holder 43 having cage opening 44, locking cap 45, one or more bone screw hole 46, and anti-migration features, e.g., serrations 47. As seen in FIG. 13, endplate 50 may comprise fusion aperture 48, having a generally oval geometry including a major diameter (D4) and a minor diameter (D5). In various embodiments, the major diameter (D4) of fusion aperture 48 may be about 0.9 cm and about 1.1 cm, and the minor diameter (D3) may be about 0.55 cm and about 0.70 cm. In this configuration, anti-rotation slots 49 may be oriented in a configuration similar to anti-rotation slots 29 to engage with the general shape of the corresponding biocompatible cage, e.g., the biocompatible pyramesh cage.

FIG. 14 illustrates a multi-level implant 100 in an installed configuration. In this embodiment, upper (towards cranial direction) endplate 20 may engage with the inferior surface of the adjacent upper vertebrae 70 and lower (towards caudal direction) endplate 20 may engage with the superior surface of the adjacent lower vertebrae 80. Once positioned within the gap between the vertebrae bone screw 60 may be screwed into the ventral surface of superior vertebrae 70 and inferior vertebrae 80 at an appropriate angulation. In various embodiments, biocompatible cage 10 may extend for a distance that is sufficient to span more than one vertebral level, e.g., two levels, three levels etc. In use, a surgeon may trim the biocompatible cage 10 to an appropriate length in view of a particular patient's specific needs. In this way, embodiments in accordance with the disclosure herein may be customized to span various lengths. In the installed state, locking cap 25 may be inserted and oriented to a locked position to prevent backing out of bone screw 60 post insertion. It should be understood to those skilled in the art that different sizes, different shapes and geometries of biocompatible cages and endplates of the present disclosure may be used. In various embodiments, the present multi-level implant may include a kit having a plurality of different size and shape endplates that are differently inclined or angled at each of the bone contacting surfaces and/or anterior plates to accommodate particular patients' spinal anatomy.

Figure 15:
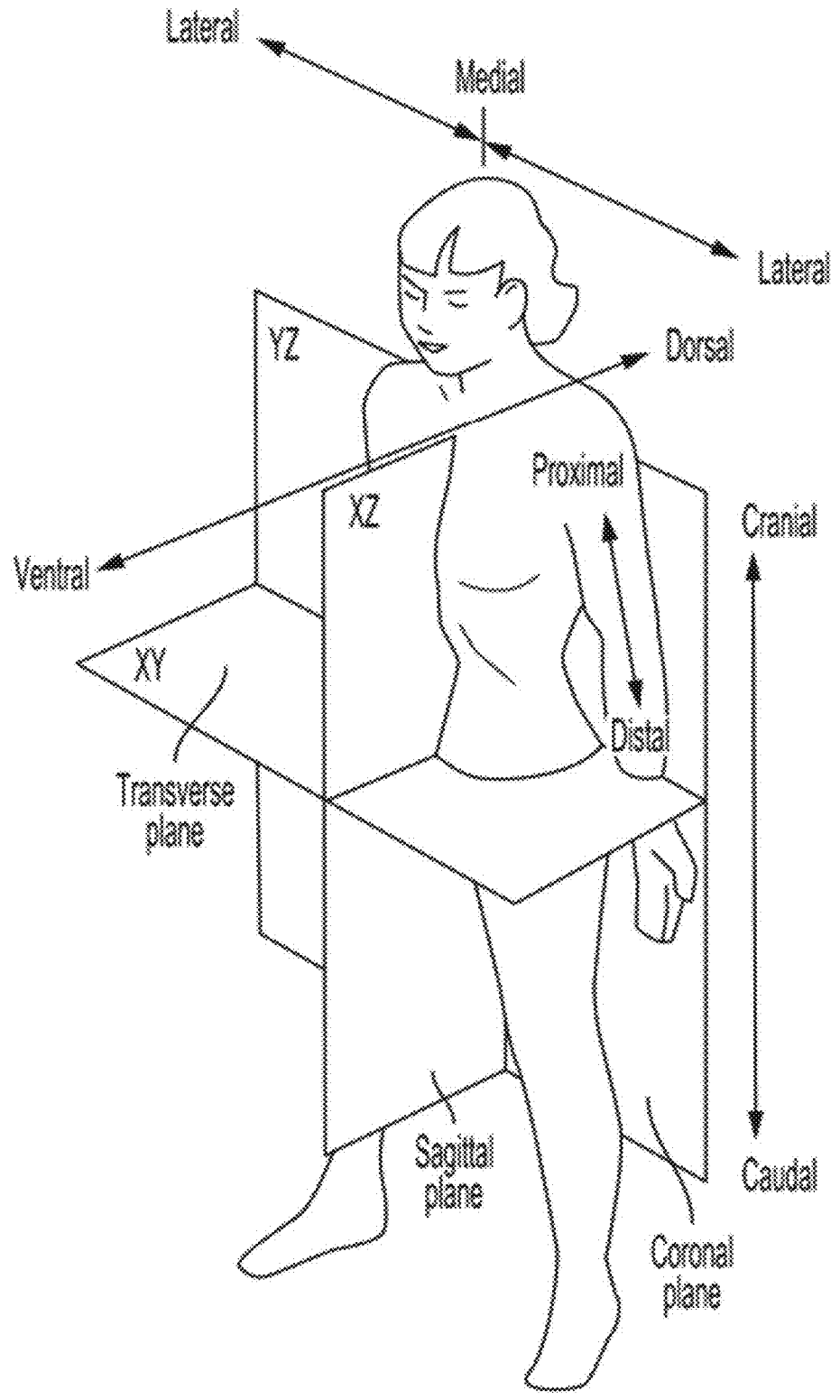
FIG. 15 depicts a reference diagram of the human spine.
Figure 16:
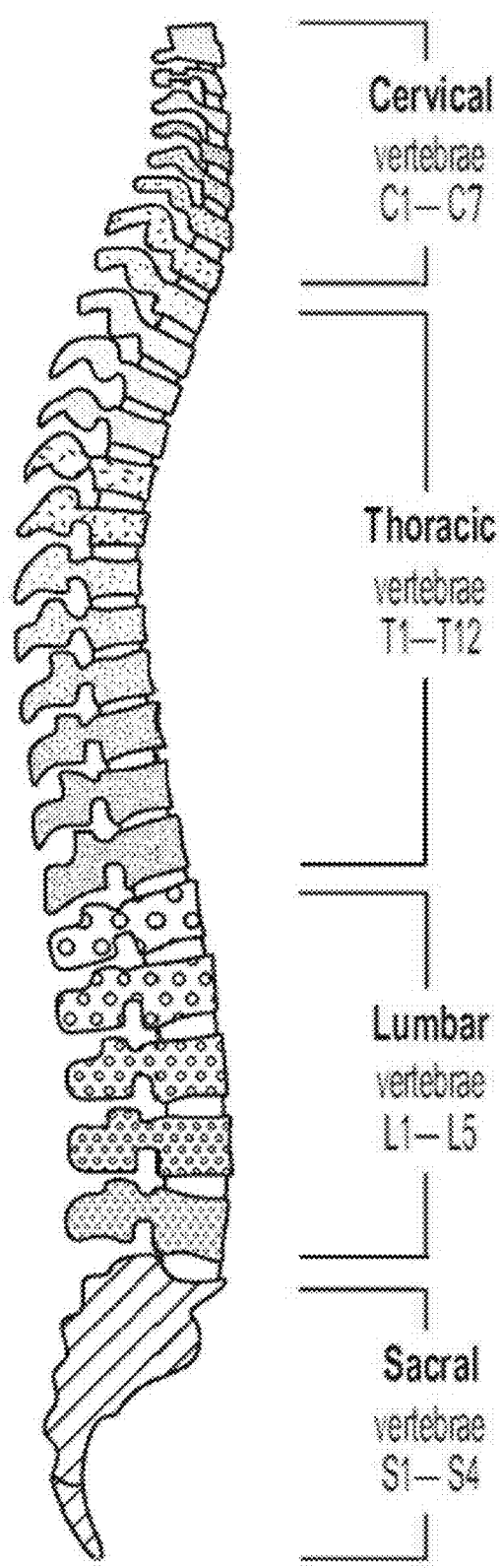
FIG. 16 depicts a reference diagram of various anatomical planes of the human body.

FIG. 15 is a reference drawing showing various planes and reference directions of which the various disclosed implant embodiments may move in or act in with reference to a patient. FIG. 16 is a reference drawing showing the human spine of which various disclosed implant embodiments may be installed in. The human spine, as depicted in FIG. 16, consists of a stack of 33 curved vertebrae that are structurally divided into five regions, namely, cervical region (C1-C7), thoracic region (T1-T12), lumbar region (L1-L5) and, the fused sacrum and coccyx regions. Towards the bottom of the spine, the vertebrae are larger because the spine supports heavier loads of the body in this area. The cervical vertebrae, forming the neck area, are relatively small to promote flexibility of the head and because they support smaller loads relative to the thoracic and lumbar regions. Just below the cervical vertebrae are the thoracic vertebrae, which form the upper back. The thoracic vertebrae are larger than the cervical vertebrae and increase in size from top towards bottom. Below the thoracic region lies the lumbar vertebrae, which are even larger and support the weight of the entire upper body. Relative motion in the spine may also vary along the length of the spinal column, as the cervical vertebra have a greater range of motion than the lower lumbar vertebra.

It should be understood that various aspects disclosed herein may be combined in different combinations than the combinations specifically presented in the description and accompanying drawings. For example, features, functionality, and components from one embodiment may be combined with another embodiment and vice versa unless the context clearly indicates otherwise. Similarly, features, functionality, and components may be omitted unless the context clearly indicates otherwise. It should also be understood that, depending on the example, certain acts or events of any of the processes or methods described herein may be performed in a different sequence, may be added, merged, or left out altogether (e.g., all described acts or events may not be necessary to carry out the techniques).

Unless otherwise specifically defined herein, all terms are to be given their broadest possible interpretation including meanings implied from the specification as well as meanings understood by those skilled in the art and/or as defined in dictionaries, treatises, etc. It must also be noted that, as used in the specification and the appended claims, the singular forms "a," "an" and "the" include plural referents unless otherwise specified, and that the terms "comprises" and/or "comprising," when used in this specification, specify the presence of stated features, elements, and/or components, but do not preclude the presence or addition of one or more other features, steps, operations, elements, components, and/or groups thereof.

Without excluding further possible embodiments, certain example embodiments are summarized in the following clauses:

Clause 1: A multi-level vertebral implant, comprising: a biocompatible cage; and a first endplate and a second endplate that each comprise: (i) a bone contacting surface that is inclined with respect to a supporting surface disposed opposite from the bone contacting surface; (ii) a plurality of anti-migration features extending from each bone contacting surface and being configured to contact an adjacent vertebrae, respectively; (iii) a cage holder extending away from each support surface, each cage holder comprising a hollow protrusion defining a fusion aperture that extends through the bone contacting surface and supporting surface of each respective endplate; (iv) an anterior plate extending orthogonally from each bone contacting surface and having at least one bone screw aperture configured to support a bone screw for anchoring into a ventral surface of a corresponding adjacent vertebrae; and (v) a plurality of anti-rotation slots disposed around each corresponding cage holder and extending through the bone contacting surface and supporting surface of each respective endplate; wherein the biocompatible cage comprises a body that extends in a longitudinal direction from a first end to a second end and has a hollow interior, wherein the first end of the body is configured to couple to the cage holder of the first endplate and the second end of the body is configured to couple to the cage holder of the second endplate, wherein the first end of the body comprises a plurality of protrusions configured to interface with the anti-rotation slots of the first endplate and the second end of the body comprises a plurality of protrusions configured to interface with the anti-rotation slots of the second endplate to thereby suppress radial movement of the biocompatible cage, and wherein the body comprises a mesh pattern including a plurality of apertures extending through a sidewall of the body that are configured to facilitate bone growth and fusion.

Clause 2: The multi-level vertebral implant of clause 1, wherein the biocompatible cage extends for a distance sufficient to span at least two vertebral levels for performing a corpectomy procedure.

Clause 3: The multi-level vertebral implant of clause 1 or clause 2, wherein each anterior plate further comprises a locking mechanism configured to keep a corresponding bone screw from backing out, the locking mechanism comprising a locking cap, a locking slot, and a groove configured to receive a notch of the locking cap.

Clause 4: The multi-level vertebral implant of clause 3, wherein the locking cap further comprises a plate, a cylinder extending longitudinally from a surface of the plate, a core extending through the cylinder and the plate, and the notch on the surface of the plate, wherein the cylinder is configured to be inserted into an aperture of the locking slot, wherein the notch is configured to be disposed in the groove of the locking slot in a locked position, and wherein the core is configured to receive an inserter tool and provide a resistive force when rotated about a longitudinal axis to displace the notch from the groove and to move the locking cap between the locked position and an unlocked position.

Clause 5: The multi-level vertebral implant of any of the preceding clauses, wherein each of the at least one bone screw apertures are configured to support a corresponding bone screw at an angle between 0° to 40° along a sagittal plane in a cranial direction and between 0° to 40° along the sagittal plane in a caudal direction.

Clause 6: The multi-level vertebral implant of any of the preceding clauses, wherein each of the at least one bone screw apertures are configured to support a corresponding bone screw at an angle between −20° to 20° along a transverse plane in a lateral direction.

Clause 7: The multi-level vertebral implant of any of the preceding clauses, wherein the fusion aperture comprises a circular, an oval, or an elliptical shape and the fusion aperture communicates with the hollow interior of the biocompatible cage to facilitate boney ingrowth and spinal fusion.

Clause 8: The multi-level vertebral implant of clause 7, wherein the circular fusion aperture comprises a diameter of about 0.25 cm and about 0.40 cm.

Clause 9: The multi-level vertebral implant of clause 7 or clause 8, wherein the oval or the elliptical fusion aperture comprises a major diameter of about 0.90 cm and about 1.10 cm, and a minor diameter of about 0.55 cm and about 0.70 cm.

Clause 10: The multi-level vertebral implant of any of the preceding clauses, wherein a centerpoint of each fusion aperture and a centerpoint of the adjacent corresponding cage holder are co-axially aligned.

Clause 11: The multi-level vertebral implant of any of the preceding clauses, wherein the cage holder is about 0.5 cm and about 1.2 cm in length.

Clause 12: The multi-level vertebral implant of any of the preceding clauses, wherein each bone contacting surface is inclined at an angle of about 0° to about 6°.

Clause 13: The multi-level vertebral implant of any of the preceding clauses, wherein the plurality of anti-migration features of the first endplate comprise a plurality of serrations that are oriented at an angle of about 15° and about 20° in a direction pointing towards the anterior plate of the first endplate and the plurality of anti-migration features of the second endplate comprise a plurality of serrations that are oriented at an angle of about 15° and about 20° in a direction pointing towards the anterior plate of the second endplate.

Clause 14: The multi-level vertebral implant of clause 13, wherein a distance between the serrations is about 0.15 cm and about 0.20 cm.

Clause 15: The multi-level vertebral implant of any of the preceding clauses, wherein the biocompatible cage comprises a circular, an oval, or an elliptical cross-section.

Clause 16: The multi-level vertebral implant of clause 15, wherein the circular cross-section comprises an inner diameter of about 0.55 cm and about 1.50 cm.

Clause 17: The multi-level vertebral implant of clause 15, wherein the oval or the elliptical cross-section comprises a major inner diameter of about 1.15 cm and about 1.50 cm, and a minor inner diameter of about 0.45 cm and about 1.05 cm.

Clause 18: The multi-level vertebral implant of any of the preceding clauses, wherein the biocompatible cage is about 1.3 cm and about 10 cm in length.

Clause 19: The multi-level vertebral implant of any of the preceding clauses, wherein the plurality of apertures defining the mesh pattern comprises a circular, triangular, diamond, square rectangular, or hexagonal shape.

Clause 20: The multi-level vertebral implant of any of the preceding clauses, wherein: exposed surfaces of each of the cage holders comprise openings configured to accommodate bone growth through the biocompatible cage and each of the first endplate and the second endplate, and the openings comprise substantially the same size and type of shape as the apertures defining the mesh like pattern of the biocompatible cage.

Clause 21: A method for treating a plurality of vertebrae regions in a patient, the method comprising: inserting a multi-level vertebral implant between an upper and lower vertebrae, wherein the multi-level vertebral implant comprises; a biocompatible cage; and a first endplate and a second endplate that each comprise: (i) a bone contacting surface that is inclined with respect to a supporting surface disposed opposite from the bone contacting surface; (ii) a plurality of anti-migration features extending from each bone contacting surface and being configured to contact an adjacent vertebrae, respectively; (iii) a cage holder extending away from each support surface, each cage holder comprising a hollow protrusion defining a fusion aperture that extends through the bone contacting surface and supporting surface of each respective endplate; and (iv) an anterior plate extending orthogonally from each bone contacting surface and having at least one bone screw aperture configured to support a bone screw for anchoring into a ventral surface of a corresponding adjacent vertebrae; wherein the biocompatible cage comprises a body that extends in a longitudinal direction from a first end to a second end; and wherein the first end of the body is configured to couple to the cage holder of the first endplate and the second end of the body is configured to couple to the cage holder of the second endplate; attaching the first endplate of the multi-level vertebral implant to the upper vertebrae in a configuration that the bone contacting surface engages with an inferior surface and the anterior plate engages with a ventral surface of the upper vertebrae; positioning the biocompatible cage within a gap between the upper and the lower vertebrae; and attaching the second endplate of the multi-level vertebral implant to the lower vertebrae in a configuration that the bone contacting surface engages with a superior surface and the anterior plate engages with a ventral surface of the lower vertebrae.

Clause 22: The method of clause 21, wherein the attaching comprises installing one or more bone screws through the one or more bone screw aperture on the anterior plate at an angle.

Clause 23: The method of clause 21 or clause 22, wherein the positioning comprises the biocompatible cage spanning more than one vertebral level.

Clause 24: A kit including a multi-level vertebral implant comprising: a biocompatible cage; and a first endplate and a second endplate that each comprise: (i) a bone contacting surface that is inclined with respect to a supporting surface disposed opposite from the bone contacting surface; (ii) a plurality of anti-migration features extending from each bone contacting surface and being configured to contact an adjacent vertebrae, respectively; (iii) a cage holder extending away from each support surface, each cage holder comprising a hollow protrusion defining a fusion aperture that extends through the bone contacting surface and supporting surface of each respective endplate; and (iv) an anterior plate extending orthogonally from each bone contacting surface and having at least one bone screw aperture configured to support a bone screw for anchoring into a ventral surface of a corresponding adjacent vertebrae; wherein the first and the second endplates comprise varying diameters and shapes of the fusion aperture; wherein the biocompatible cage comprises a body that extends in a longitudinal direction from a first end to a second end and has a hollow interior; wherein the biocompatible cage comprises varying lengths that is sufficient to span across one or more vertebral level; and wherein the first end of the body is configured to couple to the cage holder of the first endplate and the second end of the body is configured to couple to the cage holder of the second endplate.

Clause 25: The kit of clause 24, wherein the fusion aperture comprises a circular, an oval, or an elliptical shape and the fusion aperture communicates with the hollow interior of the biocompatible cage to facilitate boney ingrowth and spinal fusion.

Clause 26: The kit of clause 24 or clause 25, wherein the biocompatible cage comprises a circular, an oval, or an elliptical cross-section.

What is claimed is:

1. A multi-level vertebral implant, comprising:
a biocompatible cage; and
a first endplate and a second endplate that each comprise:
(i) a bone contacting surface that is inclined with respect to a supporting surface disposed opposite from the bone contacting surface;
(ii) a plurality of anti-migration features extending from each bone contacting surface and being configured to contact an adjacent vertebrae, respectively;
(iii) a cage holder extending away from each support surface, each cage holder comprising a hollow protrusion defining a fusion aperture that extends through the bone contacting surface and supporting surface of each respective endplate;
(iv) an anterior plate extending orthogonally from each bone contacting surface and having at least one bone screw aperture configured to support a bone screw for anchoring into a ventral surface of a corresponding adjacent vertebrae; and (v) a plurality of anti-rotation slots disposed around each corresponding cage holder and extending through the bone contacting surface and supporting surface of each respective endplate;

wherein the biocompatible cage comprises a body that extends in a longitudinal direction from a first end to a second end and has a hollow interior, wherein the first end of the body is configured to couple to the cage holder of the first endplate and the second end of the body is configured to couple to the cage holder of the second endplate, wherein the first end of the body comprises a plurality of protrusions configured to interface with the anti-rotation slots of the first endplate and the second end of the body comprises a plurality of protrusions configured to interface with the anti-rotation slots of the second endplate to thereby suppress radial movement of the biocompatible cage, wherein the body comprises a mesh pattern including a plurality of apertures extending through a sidewall of the body that are configured to facilitate bone growth and fusion, wherein the plurality of anti-migration features of the first endplate comprise a plurality of serrations that are sequentially spaced, wherein in a top down view, each serration row of the first endplate extends from a first side of the first endplate to a second side of the first endplate along a curved profile and a leading edge of each serration row is oriented at an angle in a direction pointing towards the anterior plate of the first endplate, and wherein the plurality of anti-migration features of the second endplate comprise a plurality of serrations that are sequentially spaced, wherein in a top down view, each serration row of the second endplate extends from a first side of the second endplate to a second side of the second endplate along a curved profile and a leading edge of each serration row is oriented at an angle in a direction pointing towards the anterior plate of the second endplate.

2. The multi-level vertebral implant of claim 1, wherein the biocompatible cage extends for a distance sufficient to span at least two vertebral levels for performing a corpectomy procedure.

3. The multi-level vertebral implant of claim 1, wherein each anterior plate further comprises a locking mechanism configured to keep a corresponding bone screw from backing out, the locking mechanism comprising a locking cap, a locking slot, and a groove configured to receive a notch of the locking cap.

4. The multi-level vertebral implant of claim 3, wherein the locking cap further comprises a plate, a cylinder extending longitudinally from a surface of the plate, a core extending through the cylinder and the plate, and the notch on the surface of the plate, wherein the cylinder is configured to be inserted into an aperture of the locking slot, wherein the notch is configured to be disposed in the groove of the locking slot in a locked position, and wherein the core is configured to receive an inserter tool and provide a resistive force when rotated about a longitudinal axis to displace the notch from the groove and to move the locking cap between the locked position and an unlocked position.

5. The multi-level vertebral implant of claim 1, wherein each of the at least one bone screw apertures are configured to support a corresponding bone screw at an angle between 0° to 40° along a sagittal plane in a cranial direction, between 0° to 40° along the sagittal plane in a caudal direction, and/or −20° to 20° along a transverse plane in a lateral direction.

6. The multi-level vertebral implant of claim 1, wherein the fusion aperture comprises a circular, an oval, or an elliptical shape and the fusion aperture communicates with the hollow interior of the biocompatible cage to facilitate boney ingrowth and spinal fusion.

7. The multi-level vertebral implant of claim 6, wherein the circular fusion aperture comprises a diameter of about 0.25 cm and about 0.40 cm.

8. The multi-level vertebral implant of claim 6, wherein the oval or the elliptical fusion aperture comprises a major diameter of about 0.90 cm and about 1.10 cm, and a minor diameter of about 0.55 cm and about 0.70 cm.

9. The multi-level vertebral implant of claim 1, wherein a centerpoint of each fusion aperture and a centerpoint of the adjacent corresponding cage holder are co-axially aligned.

10. The multi-level vertebral implant of claim 1, wherein the cage holder is about 0.5 cm and about 1.20 cm in length.

11. The multi-level vertebral implant of claim 1, wherein each bone contacting surface is inclined at an angle of about 0° to about 6°.

12. The multi-level vertebral implant of claim 1, wherein the leading edge of each serration row on the first endplate and the second endplate is oriented at an angle of about 15° and about 20° in a direction pointing towards the anterior plate of the first endplate and the anterior plate of the second endplate.

13. The multi-level vertebral implant of claim 12, wherein a distance between the serrations is about 0.15 cm and about 0.20 cm.

14. The multi-level vertebral implant of claim 1, wherein the biocompatible cage comprises a circular, an oval, or an elliptical cross-section.

15. The multi-level vertebral implant of claim 14, wherein the circular cross-section comprises an inner diameter of about 0.55 cm and about 1.50 cm.

16. The multi-level vertebral implant of claim 14, wherein the oval or the elliptical cross-section comprises a major inner diameter of about 1.15 cm and about 1.50 cm, and a minor inner diameter of about 0.45 cm and about 1.05 cm.

17. The multi-level vertebral implant of claim 1, wherein the biocompatible cage is about 1.3 cm and about 10 cm in length.

18. The multi-level vertebral implant of claim 1, wherein the plurality of apertures defining the mesh pattern comprises a circular, triangular, diamond, square rectangular, or hexagonal shape.

19. The multi-level vertebral implant of claim 1, wherein:

exposed surfaces of each of the cage holders comprise openings configured to accommodate bone growth through the biocompatible cage and each of the first endplate and the second endplate, and the openings comprise substantially the same size and type of shape as the apertures defining the mesh pattern of the biocompatible cage.

20. The multi-level vertebral implant of claim 1, wherein the plurality of the serration rows of the first endplate adjoin a plurality of the anti-rotation slots of the first endplate such that sidewalls of the plurality of anti-rotation slots are partially defined by the leading edge of each serration row of the first endplate, and wherein a plurality of the serration rows of the second endplate adjoin a plurality of the anti-rotation slots of the second endplate such that sidewalls of the plurality of anti-rotation slots are partially defined by the leading edge of each serration row of the second endplate.

\* \* \* \* \*